(12) United States Patent
Golubovskaya et al.

(10) Patent No.: US 11,932,703 B2
(45) Date of Patent: Mar. 19, 2024

(54) ANTI-ROR1 ANTIBODY AND ROR1-TARGETING ENGINEERED CELLS

(71) Applicant: Caribou Biosciences, Inc., Berkeley, CA (US)

(72) Inventors: Vita Golubovskaya, Pinole, CA (US); Lijun Wu, Albany, CA (US)

(73) Assignee: Caribou Biosciences, Inc.

( * ) Notice: Subject to any disclaimer, the term of this patent is extended or adjusted under 35 U.S.C. 154(b) by 0 days.

(21) Appl. No.: 18/321,655

(22) Filed: May 22, 2023

(65) Prior Publication Data
US 2023/0383009 A1 Nov. 30, 2023

Related U.S. Application Data

(60) Provisional application No. 63/365,230, filed on May 24, 2022.

(51) Int. Cl.
*C07K 16/40* (2006.01)
*C07K 14/725* (2006.01)

(52) U.S. Cl.
CPC .......... *C07K 16/40* (2013.01); *C07K 14/7051* (2013.01); *C07K 2317/24* (2013.01); *C07K 2317/565* (2013.01); *C07K 2317/622* (2013.01); *C07K 2319/03* (2013.01)

(58) Field of Classification Search
CPC ................ C07K 16/40; C07K 14/7051; C07K 2317/24; C07K 2317/565; C07K 2317/622; C07K 2319/03; C07K 16/2803; A61P 35/00; A61K 39/4611; A61K 39/4631; A61K 39/464402
See application file for complete search history.

(56) References Cited

FOREIGN PATENT DOCUMENTS

| WO | WO 2017/156479 | 9/2017 |
| WO | WO 2018/197675 | 11/2018 |
| WO | WO 2020/160050 | 8/2020 |
| WO | WO 2021/057823 | 4/2021 |

OTHER PUBLICATIONS

Rudikoff et al. Proc Natl Acad Sci USA (1982) vol. 79 p. 1979 (Year: 1982).*
Vajdos et al. (2002) 320, 415-428 (Year: 2002).*
Grupp, S.A., Kalos, M., Barrett, D., Aplenc, R., Porter, D.L., Rheingold, S.R., Teachey, D.T., Chew, A., Hauck, B., Wright, J.F., et al. (2013). Chimeric antigen receptor-modified T cells for acute lymphoid leukemia. N Engl J Med 368, 1509-1518.
Maus, M.V., Haas, A.R., Beatty, G.L., Albelda, S.M., Levine, B.L., Liu, X., Zhao, Y., Kalos, M., and June, C.H. (2013). T cells expressing chimeric antigen receptors can cause anaphylaxis in humans. Cancer Immunol Res 1, 26-31.
Maus, M.V., Grupp, S.A., Porter, D.L., and June, C.H. (2014). Antibody-modified T cells: CARs take the front seat for hematologic malignancies. Blood 123, 2625-2635.
Goluboskaya V, Wu L. Different Subsets of T Cells, Memory, Effector Functions, and CAR-T Immunotherapy. Cancers (Basel). Mar. 15, 2016;8(3). pii: E36. doi: 10.3390/cancers8030036. Review.
Dal Ferro M, Rizzo S, Rizzo E, Marano F, Luisi I, Tarasiuk O, Sblattero D. Phage Display Technology for Human Monoclonal Antibodies. Methods Enzymol 121, 332-340.
Berahovich R, Zhou H, Xu S, Wei Y, Guan J, Guan J, Harto H, Fu S, Yang K, Zhu S, Li L, Wu L, Golubovskaya V. Car-T cells based on Novel BCMA monoclonal antibody block multiple myeloma Cell growth. Cancers (Basel), 10 (9), 2018.

* cited by examiner

*Primary Examiner* — Kimberly Ballard
*Assistant Examiner* — Stacey N Macfarlane
(74) *Attorney, Agent, or Firm* — Barbara G. McClung; Olga Zimmerman

(57) ABSTRACT

The present invention is directed to a monoclonal mouse or humanized ROR1 antibody, or a single-chain variable fragment (scFv). The present invention is also directed to a mouse or humanized ROR1 chimeric antigen receptor (CAR) comprising from N-terminus to C-terminus: (i) a single-chain variable fragment (scFv) of the present invention, (ii) a transmembrane domain, (iii) at least one co-stimulatory domains, and (iv) an activating domain.

18 Claims, 8 Drawing Sheets
Specification includes a Sequence Listing.

SEQUENCE LISTING

```
Sequence total quantity: 46
SEQ ID NO: 1            moltype = AA  length = 245
FEATURE                 Location/Qualifiers
source                  1..245
                        mol_type = protein
                        organism = synthetic construct
SEQUENCE: 1
VKLVESGGGL VKPGGSLKLS CAASGFTFST YAMSWVRQTP EKRLEWVASI SSGGNTYYPD   60
SVKGRFTISR DNARHILYLQ MSSLRSEDTA MYYCARDSYY FGNSVYYAMD YWGQGTSVTV  120
SSGGGGSGGG GSGGGGSDIK MTQSPSSMYA SLGERVTITC KASQDINSYF SWFQQKPGKS  180
PKTLIYRANR LVDGVPSRFS GSGSGQDYSL TISSLEYEDM GIYYCLQYDE FPYTFGGGTK  240
LEIKR                                                              245

SEQ ID NO: 2            moltype = AA  length = 122
FEATURE                 Location/Qualifiers
source                  1..122
                        mol_type = protein
                        organism = synthetic construct
SEQUENCE: 2
VKLVESGGGL VKPGGSLKLS CAASGFTFST YAMSWVRQTP EKRLEWVASI SSGGNTYYPD   60
SVKGRFTISR DNARHILYLQ MSSLRSEDTA MYYCARDSYY FGNSVYYAMD YWGQGTSVTV  120
SS                                                                 122

SEQ ID NO: 3            moltype = AA  length = 108
FEATURE                 Location/Qualifiers
source                  1..108
                        mol_type = protein
                        organism = synthetic construct
SEQUENCE: 3
```

```
DIKMTQSPSS MYASLGERVT ITCKASQDIN SYFSWFQQKP GKSPKTLIYR ANRLVDGVPS    60
RFSGSGSGQD YSLTISSLEY EDMGIYYCLQ YDEFPYTFGG GTKLEIKR               108

SEQ ID NO: 4             moltype = AA  length = 500
FEATURE                  Location/Qualifiers
source                   1..500
                         mol_type = protein
                         organism = synthetic construct
SEQUENCE: 4
MALPVTALLL PLALLLHAAR PASVKLVESG GGLVKPGGSL KLSCAASGFT FSTYAMSWVR    60
QTPEKRLEWV ASISSGGNTY YPDSVKGRFT ISRDNARHIL YLQMSSLRSE DTAMYYCARD   120
SYYFGNSVYY AMDYWGQGTS VTVSSGGGGS GGGGSGGGGS DIKMTQSPSS MYASLGERVT   180
ITCKASQDIN SYFSWFQQKP GKSPKTLIYR ANRLVDGVPS RFSGSGSGQD YSLTISSLEY   240
EDMGIYYCLQ YDEFPYTFGG GTKLEIKRLE KPTTTPAPRP PTPAPTIASQ PLSLRPEASR   300
PAAGGAVHTR GLDFASDKPF WVLVVVGGVL ACYSLLVTVA FIIFWVRSKR SRLLHSDYMN   360
MTPRRPGPTR KHYQPYAPPR DFAAYRSRVK FSRSADAPAY QQGQNQLYNE LNLGRREEYD   420
VLDKRRGRDP EMGGKPQRRK NPQEGLYNEL QKDKMAEAYS EIGMKGERRR GKGHDGLYQG   480
LSTATKDTYD ALHMQALPPR                                              500

SEQ ID NO: 5             moltype = AA  length = 123
FEATURE                  Location/Qualifiers
source                   1..123
                         mol_type = protein
                         organism = synthetic construct
SEQUENCE: 5
EVKLVESGGG LVKPGGSLKL SCAASGFTFS TYAMSWVRQT PEKRLEWVAS ISSGGNTYYP    60
DSVKGRFTIS RDNARHILYL QMSSLRSEDT AMYYCARDSY YFGNSVYYAM DYWGQGTSVT   120
VSS                                                                123

SEQ ID NO: 6             moltype = AA  length = 107
FEATURE                  Location/Qualifiers
source                   1..107
                         mol_type = protein
                         organism = synthetic construct
SEQUENCE: 6
DIKMTQSPSS MYASLGERVT ITCKASQDIN SYFSWFQQKP GKSPKTLIYR ANRLVDGVPS    60
RFSGSGSGQD YSLTISSLEY EDMGIYYCLQ YDEFPYTFGG GTKLEIK                 107

SEQ ID NO: 7             moltype = AA  length = 501
FEATURE                  Location/Qualifiers
source                   1..501
                         mol_type = protein
                         organism = synthetic construct
SEQUENCE: 7
MALPVTALLL PLALLLHAAR PASEVKLVES GGGLVKPGGS LKLSCAASGF TFSTYAMSWV    60
RQTPEKRLEW VASISSGGNT YYPDSVKGRF TISRDNARHI LYLQMSSLRS EDTAMYYCAR   120
DSYYFGNSVY YAMDYWGQGT SVTVSSGGGG SGGGGSGGGG SDIKMTQSPS SMYASLGERV   180
TITCKASQDI NSYFSWFQQK PGKSPKTLIY RANRLVDGVP SRFSGSGSGQ DYSLTISSLE   240
YEDMGIYYCL QYDEFPYTFG GGTKLEIKLE KPTTTPAPRP PTPAPTIASQ PLSLRPEASR   300
PAAGGAVHTR GLDFASDKPF WVLVVVGGVL ACYSLLVTVA FIIFWVKRGR KKLLYIFKQP   360
FMRPVQTTQE EDGCSCRFPE EEEGGCELRV KFSRSADAPA YQQGQNQLYN ELNLGRREEY   420
DVLDKRRGRD PEMGGKPQRR KNPQEGLYNE LQKDKMAEAY SEIGMKGERR RGKGHDGLYQ   480
GLSTATKDTY DALHMQALPP R                                            501

SEQ ID NO: 8             moltype = AA  length = 245
FEATURE                  Location/Qualifiers
source                   1..245
                         mol_type = protein
                         organism = synthetic construct
SEQUENCE: 8
EVQLVESGGG LIQPGGSLRL SCAASGFTFS TYAMSWVRQA PGKGLEWVSS ISSGGNTYYA    60
DSVKGRFTIS RDNSKNTLYL QMNSLRAEDT AVYYCARDSY YFGNSVYYAM DYWGAGTTVT   120
VSSGGGGSGG GGSGGGGSDI QMTQSPSSLS ASVGDRVTIT CKASQDINSY FSWFQQKPGK   180
APKSLIYRAN RLVSGVPSRF SGSGSGTDFT LTISSLQPED FATYYCLQYD EFPYTFGGGT   240
RLEIK                                                              245

SEQ ID NO: 9             moltype = AA  length = 121
FEATURE                  Location/Qualifiers
source                   1..121
                         mol_type = protein
                         organism = synthetic construct
SEQUENCE: 9
EVQLVESGGG LIQPGGSLRL SCAASGFTFS TYAMSWVRQA PGKGLEWVSS ISSGGNTYYA    60
DSVKGRFTIS RDNSKNTLYL QMNSLRAEDT AVYYCARDSY YFGNSVYYAM DYWGAGTTVT   120
V                                                                  121

SEQ ID NO: 10            moltype = AA  length = 107
FEATURE                  Location/Qualifiers
source                   1..107
```

```
                        mol_type  = protein
                        organism  = synthetic construct
SEQUENCE: 10
DIQMTQSPSS LSASVGDRVT ITCKASQDIN SYFSWFQQKP GKAPKSLIYR ANRLVSGVPS    60
RFSGSGSGTD FTLTISSLQP EDFATYYCLQ YDEFPYTFGG GTRLEIK                 107

SEQ ID NO: 11           moltype =  AA   length = 501
FEATURE                 Location/Qualifiers
source                  1..501
                        mol_type  = protein
                        organism  = synthetic construct
SEQUENCE: 11
MALPVTALLL PLALLLHAAR PASEVQLVES GGGLIQPGGS LRLSCAASGF TFSTYAMSWV    60
RQAPGKGLEW VSSISSGGNT YYADSVKGRF TISRDNSKNT LYLQMNSLRA EDTAVYYCAR   120
DSYYFGNSVY YAMDYWGAGT TVTVSSGGGG SGGGGSGGGG SDIQMTQSPS SLSASVGDRV   180
TITCKASQDI NSYFSWFQQK PGKAPKSLIY RANRLVSGVP SRFSGSGSGT DFTLTISSLQ   240
PEDFATYYCL QYDEFPYTFG GGTRLEIKLE KPTTTPAPRP PTPAPTIASQ PLSLRPEASR   300
PAAGGAVHTR GLDFASDKPF WVLVVVGGVL ACYSLLVTVA FIIFWVKRGR KKLLYIFKQP   360
FMRPVQTTQE EDGCSCRFPE EEEGGCELRV KFSRSADAPA YQQGQNQLYN ELNLGRREEY   420
DVLDKRRGRD PEMGGKPQRR KNPQEGLYNE LQKDKMAEAY SEIGMKGERR RGKGHDGLYQ   480
GLSTATKDTY DALHMQALPP R                                            501

SEQ ID NO: 12           moltype =  AA   length = 245
FEATURE                 Location/Qualifiers
source                  1..245
                        mol_type  = protein
                        organism  = synthetic construct
SEQUENCE: 12
QVQLVESGGG VVQPGRSLRL SCAASGFTFS TYAMSWVRQA PGKGLEWVAS ISSGGNTYYP    60
DSVKGRFTIS RDNSKNTLYL QMNSLRAEDT AVYYCARDSY YFGNSVYYAM DYWGAGTTVT   120
VSSGGGGSGG GGSGGGGSDI QMTQSPSSLS ASVGDRVTIT CKASQDINSY FSWFQQKPGK   180
APKSLIYRAN RLVSGVPSRF SGSGSGTDFT LTISSLQPED FATYYCLQYD EFPYTFGGGT   240
RLEIK                                                              245

SEQ ID NO: 13           moltype =  AA   length = 123
FEATURE                 Location/Qualifiers
source                  1..123
                        mol_type  = protein
                        organism  = synthetic construct
SEQUENCE: 13
QVQLVESGGG VVQPGRSLRL SCAASGFTFS TYAMSWVRQA PGKGLEWVAS ISSGGNTYYP    60
DSVKGRFTIS RDNSKNTLYL QMNSLRAEDT AVYYCARDSY YFGNSVYYAM DYWGAGTTVT   120
VSS                                                                123

SEQ ID NO: 14           moltype =  AA   length = 107
FEATURE                 Location/Qualifiers
source                  1..107
                        mol_type  = protein
                        organism  = synthetic construct
SEQUENCE: 14
DIQMTQSPSS LSASVGDRVT ITCKASQDIN SYFSWFQQKP GKAPKSLIYR ANRLVSGVPS    60
RFSGSGSGTD FTLTISSLQP EDFATYYCLQ YDEFPYTFGG GTRLEIK                 107

SEQ ID NO: 15           moltype =  AA   length = 501
FEATURE                 Location/Qualifiers
source                  1..501
                        mol_type  = protein
                        organism  = synthetic construct
SEQUENCE: 15
MALPVTALLL PLALLLHAAR PASQVQLVES GGGVVQPGRS LRLSCAASGF TFSTYAMSWV    60
RQAPGKGLEW VASISSGGNT YYPDSVKGRF TISRDNSKNT LYLQMNSLRA EDTAVYYCAR   120
DSYYFGNSVY YAMDYWGAGT TVTVSSGGGG SGGGGSGGGG SDIQMTQSPS SLSASVGDRV   180
TITCKASQDI NSYFSWFQQK PGKAPKSLIY RANRLVSGVP SRFSGSGSGT DFTLTISSLQ   240
PEDFATYYCL QYDEFPYTFG GGTRLEIKLE KPTTTPAPRP PTPAPTIASQ PLSLRPEASR   300
PAAGGAVHTR GLDFASDKPF WVLVVVGGVL ACYSLLVTVA FIIFWVKRGR KKLLYIFKQP   360
FMRPVQTTQE EDGCSCRFPE EEEGGCELRV KFSRSADAPA YQQGQNQLYN ELNLGRREEY   420
DVLDKRRGRD PEMGGKPQRR KNPQEGLYNE LQKDKMAEAY SEIGMKGERR RGKGHDGLYQ   480
GLSTATKDTY DALHMQALPP R                                            501

SEQ ID NO: 16           moltype =  AA   length = 245
FEATURE                 Location/Qualifiers
source                  1..245
                        mol_type  = protein
                        organism  = synthetic construct
SEQUENCE: 16
QVQLVESGGG VVQPGRSLRL SCAASGFTFS TYAMSWVRQA PGKGLEWVAS ISSGGNTYYP    60
DSVKGRFTIS RDNSKNTLYL QMNSLRAEDT AVYYCARDSY YFGNSVYYAM DYWGAGTTVT   120
VSSGGGGSGG GGSGGGGSDI QMTQSPSSLS ASVGDRVTIT CKASQDINSY FSWYQQKPGK   180
APKLLIYRAN RLVTGVPSRF SGSGSGTDFT FTISSLQPED IATYYCLQYD EFPYTFGGGT   240
```

```
RLEIK                                                                    245

SEQ ID NO: 17           moltype = AA  length = 123
FEATURE                 Location/Qualifiers
source                  1..123
                        mol_type = protein
                        organism = synthetic construct
SEQUENCE: 17
QVQLVESGGG VVQPGRSLRL SCAASGFTFS TYAMSWVRQA PGKGLEWVAS ISSGGNTYYP      60
DSVKGRFTIS RDNSKNTLYL QMNSLRAEDT AVYYCARDSY YFGNSVYYAM DYWGAGTTVT     120
VSS                                                                   123

SEQ ID NO: 18           moltype = AA  length = 107
FEATURE                 Location/Qualifiers
source                  1..107
                        mol_type = protein
                        organism = synthetic construct
SEQUENCE: 18
DIQMTQSPSS LSASVGDRVT ITCKASQDIN SYFSWYQQKP GKAPKLLIYR ANRLVTGVPS      60
RFSGSGSGTD FTFTISSLQP EDIATYYCLQ YDEFPYTFGG GTRLEIK                   107

SEQ ID NO: 19           moltype = AA  length = 501
FEATURE                 Location/Qualifiers
source                  1..501
                        mol_type = protein
                        organism = synthetic construct
SEQUENCE: 19
MALPVTALLL PLALLLHAAR PASQVQLVES GGGVVQPGRS LRLSCAASGF TFSTYAMSWV      60
RQAPGKGLEW VASISSGGNT YYPDSVKGRF TISRDNSKNT LYLQMNSLRA EDTAVYYCAR     120
DSYYFGNSVY YAMDYWGAGT TVTVSSGGGG SGGGGSGGGG SDIQMTQSPS SLSASVGDRV     180
TITCKASQDI NSYFSWYQQK PGKAPKLLIY RANRLVTGVP SRFSGSGSGT DFTFTISSLQ     240
PEDIATYYCL QYDEFPYTFG GGTRLEIKLE KPTTTPAPRP PTPAPTIASQ PLSLRPEASR     300
PAAGGAVHTR GLDFASDKPF WVLVVVGGVL ACYSLLVTVA FIIFWVKRGR KKLLYIFKQP     360
FMRPVQTTQE EDGCSCRFPE EEEGGCELRV KFSRSADAPA YQQGQNQLYN ELNLGRREEY     420
DVLDKRRGRD PEMGGKPQRR KNPQEGLYNE LQKDKMAEAY SEIGMKGERR RGKGHDGLYQ     480
GLSTATKDTY DALHMQALPP R                                              501

SEQ ID NO: 20           moltype = DNA  length = 735
FEATURE                 Location/Qualifiers
source                  1..735
                        mol_type = other DNA
                        organism = synthetic construct
SEQUENCE: 20
gtgaagctgg tggagtctgg gggaggctta gtgaagcctg agggtccct gaaactctcc       60
tgtgcagcct ctggattcac tttcagtacc tatgccatgt cttgggttcg ccagactcca     120
gagaagaggc tggagtgggt cgcatccatt agtagtggtg gtaacaccta ctatccagac     180
agtgtgaagg gccgattcac catctccaga gataatgcca ggcacatcct gtacctgcaa     240
atgagcagtc tgaggtctga ggacacggcc atgtattact gtgcaagaga ttcttattac     300
ttcggtaata gcgtttacta tgctatggac tactggggtc aaggaacctc agtcaccgtc     360
tcctcaggtg gcggtggttc tggtggcggt ggttctggtg gcggtggttc tgacatcaag     420
atgacccagt ctccatcttc catgtatgca tctctaggag agagagtcac tatcacttgc     480
aaggcgagtc aggacattaa tagctatttt agctggttcc agcaaaaacc agggaaatct     540
cctaagaccc tgatctatcg tgcaaataga ttggtagatg ggtcccatc aaggttcagt     600
ggcagtggat ctgggcagga ttattctctc accatcagca gcctggagta tgaagatatg     660
ggaatttatt attgtctaca gtatgatgag tttccgtaca cgttcggagg ggggaccaaa     720
ctggaaataa aacgg                                                      735

SEQ ID NO: 21           moltype = DNA  length = 63
FEATURE                 Location/Qualifiers
source                  1..63
                        mol_type = other DNA
                        organism = synthetic construct
SEQUENCE: 21
atggcttac cagtgaccgc cttgctcctg ccgctggcct tgctgctcca cgccgccagg       60
ccg                                                                    63

SEQ ID NO: 22           moltype = AA  length = 21
FEATURE                 Location/Qualifiers
source                  1..21
                        mol_type = protein
                        organism = synthetic construct
SEQUENCE: 22
MALPVTALLL PLALLLHAAR P                                                21

SEQ ID NO: 23           moltype = AA  length = 245
FEATURE                 Location/Qualifiers
source                  1..245
                        mol_type = protein
                        organism = synthetic construct
```

```
SEQUENCE: 23
EVKLVESGGG LVKPGGSLKL SCAASGFTFS TYAMSWVRQT PEKRLEWVAS ISSGGNTYYP    60
DSVKGRFTIS RDNARHILYL QMSSLRSEDT AMYYCARDSY YFGNSVYYAM DYWGQGTSVT   120
VSSGGGGSGG GGSGGGGSDI KMTQSPSSMY ASLGERVTIT CKASQDINSY FSWFQQKPGK   180
SPKTLIYRAN RLVDGVPSRF SGSGSGQDYS LTISSLEYED MGIYYCLQYD EFPYTFGGGT   240
KLEIK                                                               245

SEQ ID NO: 24               moltype = DNA    length = 141
FEATURE                     Location/Qualifiers
source                      1..141
                            mol_type = other DNA
                            organism = synthetic construct
SEQUENCE: 24
aagcccacca cgacgccagc gccgcgacca ccaacaccgg cgcccaccat cgcgtcgcag    60
cccctgtccc tgcgcccaga ggcgagccgg ccagcggcgg ggggcgcagt gcacacgagg   120
gggctggact cgccagtga  t                                             141

SEQ ID NO: 25               moltype = AA    length = 47
FEATURE                     Location/Qualifiers
source                      1..47
                            mol_type = protein
                            organism = synthetic construct
SEQUENCE: 25
KPTTTPAPRP PTPAPTIASQ PLSLRPEASR PAAGGAVHTR GLDFASD                  47

SEQ ID NO: 26               moltype = DNA    length = 204
FEATURE                     Location/Qualifiers
source                      1..204
                            mol_type = other DNA
                            organism = synthetic construct
SEQUENCE: 26
ttttgggtgc tggtggtggt tggtggagtc ctggcttgct atagcttgct agtaacagtg    60
gcctttatta ttttctgggt gaggagtaag aggagcaggc tcctgcacag tgactacatg   120
aacatgactc cccgccgccc cgggcccacc cgcaagcatt accagcccta tgccccacca   180
cgcgacttcg cagcctatcg ctcc                                          204

SEQ ID NO: 27               moltype = AA    length = 68
FEATURE                     Location/Qualifiers
source                      1..68
                            mol_type = protein
                            organism = synthetic construct
SEQUENCE: 27
FWVLVVVGGV LACYSLLVTV AFIIFWVRSK RSRLLHSDYM NMTPRRPGPT RKHYQPYAPP    60
RDFAAYRS                                                             68

SEQ ID NO: 28               moltype = DNA    length = 339
FEATURE                     Location/Qualifiers
source                      1..339
                            mol_type = other DNA
                            organism = synthetic construct
SEQUENCE: 28
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatgggggg aaagccgcag agaaggaaga accctcagga aggcctgtac   180
aatgaactgc agaaagataa gatggcggag gcctacagtg agattgggat gaaaggcgag   240
cgccggaggg gcaagggggca cgatggcctt taccaggtc tcagtacagc caccaaggac   300
acctacgacg cccttcacat gcaggccctg ccccctcgc                          339

SEQ ID NO: 29               moltype = AA    length = 113
FEATURE                     Location/Qualifiers
source                      1..113
                            mol_type = protein
                            organism = synthetic construct
SEQUENCE: 29
RVKFSRSADA PAYQQGQNQL YNELNLGRRE EYDVLDKRRG RDPEMGGKPQ RRKNPQEGLY    60
NELQKDKMAE AYSEIGMKGE RRRGKGHDGL YQGLSTATKD TYDALHMQAL PPR           113

SEQ ID NO: 30               moltype = DNA    length = 1503
FEATURE                     Location/Qualifiers
source                      1..1503
                            mol_type = other DNA
                            organism = synthetic construct
SEQUENCE: 30
atggcctac cagtgaccgc cttgctcctg ccgctggcct tgctgctcca cgccgcagg      60
ccggctagcg tgaagctggt ggagtctggg ggaggcttag tgaagcctgg agggtccctg   120
aaactctcct gtcagcctc tggattcact ttcagtacct atgccatgtc ttgggttcgc   180
cagactccag agaagaggct ggagtgggtc gcatccatta gtagtggtgg taacacctac   240
tatccagaca gtgtgaaggg ccgattcacc atctccagag ataatgccag gcacatcctg   300
tacctgcaaa tgagcagtct gaggtctgag gacacggcca tgtattactg tgcaagagat   360
```

```
tcttattact tcggtaatag cgtttactat gctatggact actggggtca aggaacctca    420
gtcaccgtct cctcaggtgg cggtggttcc ggtggcggtg ttctggtgg cggtggttct     480
gacatcaaga tgacccagtc tccatcttcc atgtatgcat ctctaggaga gagagtcact    540
atcacttgca aggcgagtca ggacattaat agctatttta gctggttcca gcaaaaacca    600
gggaaactct ctaagaccct gatctatcgt gcaaatagat tggtagatgg ggtcccatca    660
aggttcagtg gcagtggatc tgggcaggat tattctctca ccatcagcag cctggagtat    720
gaagatatgg gaatttatta ttgtctacag tatgatgagt ttccgtacac gttcggaggg    780
gggaccaaac tggaaataaa acggctcgag aagcccacca cgacgccagc gccgcgacca    840
ccaacaccgg cgcccaccat cgcgtcgcag ccctgtccc tgcgcccaga ggcgagccgg     900
ccagcggcgg ggggcgcagt gcacacgagg gggctggact cgccagtga taagcccttt    960
tgggtgctgg tggtggttgg tggagtcctg gcttgctata gcttgctagt aacagtggcc    1020
tttattattt tctgggtgag gagtaagagg agcaggctcc tgcacagtga ctacatgaac    1080
atgactcccc gccgccccgg gccaccgcg aagcattacc agccctatgc cccaccacgc     1140
gacttcgcag cctatcgctc cagagtgaag ttcagcagga cgcagacgc ccccgcgtac     1200
cagcagggcc agaaccagct ctataacgag ctcaatctag gacgaagaga ggagtacgat    1260
gttttggaca gagacgtgg ccgggaccct gagatggggg gaaagccgca gagaaggaag     1320
aaccctcagg aaggcctgta caatgaactg cagaaagata gatggcgga ggcctacagt     1380
gagattggga tgaaaggcga gcgccggagg ggcaaggggc acgatggcct ttaccagggt    1440
ctcagtacag ccaccaagga cacctacgac gcccttcaca tgcaggccct gccccctcgc    1500
taa                                                                   1503

SEQ ID NO: 31          moltype = DNA  length = 1505
FEATURE                Location/Qualifiers
source                 1..1505
                       mol_type = other DNA
                       organism = synthetic construct
SEQUENCE: 31
atggccttac cagtgaccgc cttgctcctg ccgctggcct tgctgctcca cgccgccagg    60
ccggctagcg aagtgaagct tgtcgaatcc ggcggtggat tggttaaacc aggcggaagt    120
ttgaaactga gttgtgctgc ttctggtttt acctttagca catacgctat gtcctgcatg    180
aggcagacgc cggagaaacg attggagtgg tagcatctat ttcttctggc ggcaatactt    240
attaccctga cagcgtgaaa ggccggttca ctatttctcg agataatgcg cggcacatac    300
tctatctcca gatgtcttct ctccgctcag aggatacagc gatgtactat tgtgcaaggg    360
atagttacta tttcggaaac tctgtgtatt atgcaatgga ttactggggt cagggaactt    420
cagtcacagt aagctcaggt gggggaggaa gcggcggttgg cggctcaggg gcaggtggat    480
ctgatattaa aatgactcag tctccatcaa gcatgtacgc ctctctggga gagcgagtta    540
ctattacctg taaagcatca agagatatta ctcttatttt agttggtttt caacaaaagc    600
ctggaaaatc acctaaaact ttgatttata gagccaatag gcttgtggat ggtgtaccta    660
gtcggtttag cggctcaggg tcaggccaag actattcttt gaccatctct tctctggggt    720
atgaggacat gggaatctat tactgtcttc agtacgatga gttcccctat acgtttggtg    780
gaggcactaa attggagatt aaactcgaga agcccaccac gacgccagcg ccgcgaccac    840
caacaccggc gcccaccatc gcgtcgcagc ccctgtccc tgcgcccaga ggcgagccggc    900
cagcggcggg gggcgcagtg cacacgaggg gctggactc cgccagtgat aagcccttt    960
gggtgctggt ggtggttggt ggagtcctgg cttgctatag cttgctagta acagtggcct    1020
ttattatttt ctgggtgaaa cggggcagaa agaaactcct gtatatattc aaacaaccat    1080
ttatgagacc agtacaaact actcaagagg aagatggctg tagctgccga tttccagaag    1140
aagaagaagg aggatgtgaa ctgagagtga agttcagcag gacgcagac gccccccgcgt    1200
accagcaggg ccagaaccag ctctataacg agctcaatct aggacgaaga ggagagtacg    1260
atgtttttgga caagagacgt ggccgggacc tgagatgggg ggaaagccg cagagaagga    1320
agaaccctca ggaaggcctc tacaatgaac tgcagaaaga taagatggcg gaggcctaca    1380
gtgagattgg gatgaaaggc gagcgccgga ggggcaaggg gcacgatggc ctttaccagg    1440
gtctcagtac agcaccaag gacacctacg acgcccttca tgcaggcc ctgccccctc       1500
gctaa                                                                 1505

SEQ ID NO: 32          moltype = DNA  length = 126
FEATURE                Location/Qualifiers
source                 1..126
                       mol_type = other DNA
                       organism = synthetic construct
SEQUENCE: 32
aaacggggca gaaagaaact cctgtatata ttcaaacaac catttatgag accagtacaa    60
actactcaag aggaagatgg ctgtagctgc cgatttccag aagaagaaga aggaggatgt    120
gaactg                                                                126

SEQ ID NO: 33          moltype = AA  length = 42
FEATURE                Location/Qualifiers
source                 1..42
                       mol_type = protein
                       organism = synthetic construct
SEQUENCE: 33
KRGRKKLLYI FKQPFMRPVQ TTQEEDGCSC RFPEEEEGGC EL                         42

SEQ ID NO: 34          moltype = DNA  length = 735
FEATURE                Location/Qualifiers
source                 1..735
                       mol_type = other DNA
                       organism = synthetic construct
SEQUENCE: 34
gaagtacagc ttgttgaatc aggtggtggt cttattcagc caggaggctc cttgcgactg    60
```

```
agctgtgccg cttctgggtt cacctttagc acttacgcaa tgagttgggt ccgacaagcc    120
ccaggtaagg gattggaatg ggtaagttcc atttccagcg gagggaacac ttattacgcc    180
gattctgtga aaggacgctt tactatatcc cgagacaata gtaaaaacac attgtatttg    240
caaatgaact ctttgagggc cgaggacact gccgtctact attgtgcccg cgacagctat    300
tatttcggca actctgtgta ttacgcgatg gattactggg gtgccggcac aactgtcacc    360
gtttcatctg gcggaggagg cagtggcgga gggggctcag gcggtggtgg aagtgatatt    420
caaatgaccc aatcaccctc ttcattgtct gcaagcgtag gtgaccgagt cacgataacc    480
tgcaaagcct ctcaagatat taattcatac ttttcttggt tcaacaaaa accgggaaag    540
gcgcctaagt cattgattta ccgcgcgaac cggttggtat caggagtacc gtcaagattc    600
tcagggagtg ggtcaggcac agatttcaca ctcactattt cttccttgca acctgaagac    660
ttcgcaacct attattgctt gcagtatgat gagtttccgt acactttcgg ggggggtaca    720
aggctggaga tcaaa                                                      735

SEQ ID NO: 35       moltype = DNA  length = 1506
FEATURE             Location/Qualifiers
source              1..1506
                    mol_type = other DNA
                    organism = synthetic construct
SEQUENCE: 35
atggccttac cagtgaccgc cttgctcctg ccgctggcct tgctgctcca cgccgccagg     60
ccggctagcg aagtacagct tgttgaatca ggtggtggtc ttattcagcc aggaggctcc    120
ttgcgactga gctgtgccgc ttctgggttc acctttagca cttacgcaat gagttgggtc    180
cgacaagccc caggtaaggg attggaatgg gtaagttcca tttccagcgg agggaacact    240
tattacgccg attctgtgaa aggacgcttt actatatccc gagacaatag taaaaacaca    300
ttgtatttgc aaatgaactc tttgagggcc gaggacactg ccgtctacta ttgtgcccgc    360
gacagctatt atttcggcaa ctctgtgtat tacgcgatgg attactgggg tgccggcaca    420
actgtcaccg tttcatctgg cggaggaggc agtggcggag ggggctcagg cggtggtgga    480
agtgatattc aaatgaccca atcaccctct tcattgtctg caagcgtagg tgaccgagtc    540
acgataacct gcaaagcctc tcaagatatt aattcatact tttcttggtt caacaaaaa    600
ccgggaaagg cgcctaagtc attgatttac cgcgcgaacc ggttggtatc aggagtaccg    660
tcaagattct cagggagtgg gtcaggcaca gatttcacac tcactatttc ttccttgcaa    720
cctgaagact tcgcaaccta ttattgcttg cagtatgatg agtttccgta cactttcggg    780
ggggtacaa ggctggagat caaactcgag aagcccacca cgacgccagc gccgcgacca    840
ccaacaccgg cgcccaccat cgcgtcgcag cccctgtccc tgcgcccaga ggcgagccgg    900
ccagcggccg ggggcgcagt gcacacgagg gggctggact cgccagtgac taagcccttt    960
tgggtgctgg tggtggttgg tggagtcctg gcttgctata gcttgctagt aacagtggcc   1020
tttattattt tctgggtgaa acggggcaga aagaaactcc tgtatatatt caaacaacca   1080
tttatgagac cagtacaaac tactcaagag gaagatggct gtagctgccg atttccagaa   1140
gaagaagaag gaggatgtga actgagagtg aagttccgca gcgccccgcg taccagcagg   1200
gccagaacca gctctataac gagctcaatc taggacgaag agaggagtac gatgttttgg   1260
acaagagacg tggccgggac cctgagatgg ggggaaagcc gcagagaagg aagaaccctc   1320
aggaaggcct ctacaatgaa ctgcagaaaa taagatggcg gaggcctaca gtgagattgg   1380
ggatgaaagg cgagcgccgg aggggcaagg ggcacgatgg cctttaccag ggtctcagta   1440
cagccaccaa ggacacctac gacgcccttc acatgcaggc cctgcccct cgctaa        1506

SEQ ID NO: 36       moltype = DNA  length = 735
FEATURE             Location/Qualifiers
source              1..735
                    mol_type = other DNA
                    organism = synthetic construct
SEQUENCE: 36
caggtacaat tggtagagtc cggcggaggg gttgttcagc caggacggtc cttgcggttg     60
tcttgtgctg cgtcaggatt cacattctca acgtacgcga tgtcttgggt gcgccaagct    120
cccgtaaagg ggctggaatg ggtggcctca atctcatctg gagggaacac ttactaccct    180
gatagtgtta aggtcgcttt actatctca agggacaata gcaagaatac cttgtatctg    240
caaatgaact cacttagagc agaggacaca gcggtatatt actgtgctag agactcatat    300
tatttcggca actccgttta ttacgcgatg gattactggg gcgcagggac tacggtaact    360
gtatcttctg gtggtggagg gtctgggggc ggggtagtg gcgccggtgg cagtgacatc    420
cagatgacac agtctccgtc ttcattgagt gcaagcgtcg gcgatcggtt taccattacg    480
tgtaaggcaa gtcaggacat taacagttat ttttcatggt tcaacaaaaa gcctggaaaa    540
gcgccgaaat cactcattta ccgagctaat aggcttgtct ctggcgttcc gtctcgcttc    600
agtggaagtg ggagcggtac tgattttacc ctcaccatat caagccttca accggaggat    660
tttgccacgt actattgtct ccagtacgat gaatttccat atacgtttgg cggcgggact    720
cgcttggaga ttaaa                                                      735

SEQ ID NO: 37       moltype = DNA  length = 1506
FEATURE             Location/Qualifiers
source              1..1506
                    mol_type = other DNA
                    organism = synthetic construct
SEQUENCE: 37
atggccttac cagtgaccgc cttgctcctg ccgctggcct tgctgctcca cgccgccagg     60
ccggctagcg aggtacaatt ggtagagtcc gcggaggg ttgttcagc caggacggtc    120
ttgcggttgt cttgtgctgc gtcaggatta cattctcaa cgtacgcgat gtcttgggtg    180
cgccaagctc ccgtaaaggg gctggaatgg gtggcctcaa tctcatctgg agggaacact    240
tactaccctg atagtgttaa aggtcgcttt actatctcaa gggacaatag caagaatacc    300
ttgtatctgc aaatgaactc acttagagca gaggacacag gtatattac tgtgctaga    360
gactcatatt atttcggcaa ctccgtttat tacgcgatgg attactgggg cgcagggact    420
```

```
acggtaactg tatcttctgg tggtggaggg tctgggggcg ggggtagtgg cggcggtggc    480
agtgacatcc agatgacaca gtctccgtct tcattgagtg caagcgtcgg cgatcgggtt    540
accattacgt gtaaggcaag tcaggacatc aacagttatt tttcatggtt tcaacaaaag    600
cctggaaaag cgccgaaatc actcatttac cgagctaata ggcttgtctc tggcgttccg    660
tctcgcttca gtggaagtgg gagcgtgact gattttcccc tcaccatatc aagccttcaa    720
ccggaggatt ttgccacgta ctattgtctc cagtacgatg aatttcccata tacgtttggc    780
ggcgggactc gcttggagat taaactcgag aagcccacca cgacgccagc gccgcgacca    840
ccaacaccgg cgcccaccat cgcgtcgcag cccctgtccc tgcgcccaga ggcgagccgg    900
ccagcggcgg ggggcgcagt gcacacgagg gggctggact tcgccagtga taagcccttt    960
tgggtgctgg tggtggttgg tggagtcctg gcttgctata gcttgctagt aacagtggcc    1020
tttattattt tctgggtgaa acggggcaga aagaaactcc tgtatatatt caaacaacca    1080
tttatgagac cagtacaaac tactcaagag gaagatggct gtagctgccg atttccagaa    1140
gaagaagaag gaggatgtga actgagagtg aagttcagca ggagcgcaga cgcccccgcg    1200
taccagcagg gccagaacca gctctataac gagctcaatc taggacgaag agaggagtac    1260
gatgttttgg acaagagacg tggccgggac cctgagatgg ggggaaagcc gcagagaagg    1320
aagaaccctc aggaaggcct ctacaatgaa ctgcagaaag ataagatggc ggaggcctac    1380
agtgagattg gatgaaaagg cgagcgccgg aggggcaagg ggcacgatgg cctttaccag    1440
ggtctcagta cagccaccaa ggacacctac gacgcccttc acatgcaggc cctgccccct    1500
cgctaa                                                               1506

SEQ ID NO: 38          moltype = DNA  length = 735
FEATURE                Location/Qualifiers
source                 1..735
                       mol_type = other DNA
                       organism = synthetic construct
SEQUENCE: 38
caggtacaac tggtggaatc cggcggggga gtagtacagc ccggacgatc tcttcgactc     60
tcatgtgcag cgtccgggtt cacttttttct acctacgcaa tgtcatgggt acgacaggcg   120
ccgggcaaag gcctcgaatg ggttgcatcc atttcatcag gaggtaatac atattatcct   180
gattcagtca agggccgatt cacgattagt cgagtaataa caagaacac tctctacttg    240
cagatgaact ccctgcgggc tgaggacacg gccgtgtatt attgcgctcg cgatagttat   300
tacttcggca attccgtata ttatgcgatg gactattggg gcgccggtac taccgtgact   360
gtttcctctg gtggggtgg gtccggggggc ggtggttcag gtggaggcgg atccgacatt    420
caaatgaccc agtctccctc aagtttgtct gcatctgttg gcgatagagt tacaataaca   480
tgcaaagcca gtcaagacat caactcatac ttctcctggt atcaacaaaa gccaggaaaa   540
gctccgaaac tgttgatcta ccgggccaac cggctggtca ctggcgtgcc atcccggttc   600
agtggcagcg aagcggaaca agatttcacg tttaccatct ctagcctcca accggaggac   660
atcgcaacat actattgcct tcagtatgat gagttcccct cactttcgg tggcggcacc   720
cgacttgaga tcaaa                                                    735

SEQ ID NO: 39          moltype = DNA  length = 1506
FEATURE                Location/Qualifiers
source                 1..1506
                       mol_type = other DNA
                       organism = synthetic construct
SEQUENCE: 39
atggccttac cagtgaccgc cttgctcctg ccgctggcct tgctgctcca cgccgccagg    60
ccggctagcc aggtacaact ggtggaatcc ggcggggga gtagtacagcc cggacgatct   120
cttcgactct catgtgcagc gtccgggttc acttttttcta cctacgcaat gtcatggta   180
cgacaggcgc cgggcaaagg cctcgaatgg gttgcatcca tttcatcagg aggtaataca   240
tattatcctg attcagtcaa gggccgattc acgattagtc gagataatag caagaacacc   300
ctctacttgc agatgaactc cctgcgggct gaggacacgg ccgtgtatta ttgcgctcgc   360
gatagttatt acttcggcaa ttccgtatat tatgcgatgg actattgggg cgccggtact   420
accgtgactt ttcctctgg tggggggtgg tccgggggcg gtggttcagg tggaggcgga    480
tccgacattc aaatgaccca gtctccctca agtttgtctg catctgttgg cgatagagtt   540
acaataacat gcaaagccag tcaagacatc aactctatct tctcctggta tcaacaaaag   600
ccaggaaaag ctccgaaact gttgatctac cgggccaacc ggctggtcac tggcgtgcca   660
tcccggttca gtggcagcgg aagcggaaca gatttcacgt ttaccatctc tagcctccaa    720
ccggaggaca tcgcaacata ctattgcctt cagtatgatg agtttcccta cactttcggt   780
ggcggcaccc gacttgagat caaactcgag aagcccacca cgacgccagc gccgcgacca    840
ccaacaccgg cgcccaccat cgcgtcgcag cccctgtccc tgcgcccaga ggcgagccgg    900
ccagcggcgg ggggcgcagt gcacacgagg gggctggact tcgccagtga taagcccttt    960
tgggtgctgg tggtggttgg tggagtcctg gcttgctata gcttgctagt aacagtggcc    1020
tttattattt tctgggtgaa acggggcaga aagaaactcc tgtatatatt caaacaacca    1080
tttatgagac cagtacaaac tactcaagag gaagatggct gtagctgccg atttccagaa    1140
gaagaagaag gaggatgtga actgagagtg aagttcagca ggagcgcaga cgcccccgcg    1200
taccagcagg gccagaacca gctctataac gagctcaatc taggacgaag agaggagtac    1260
gatgttttgg acaagagacg tggccgggac cctgagatgg ggggaaagcc gcagagaagg    1320
aagaaccctc aggaaggcct ctacaatgaa ctgcagaaag ataagatggc ggaggcctac    1380
agtgagattg gatgaaaagg cgagcgccgg aggggcaagg ggcacgatgg cctttaccag    1440
ggtctcagta cagccaccaa ggacacctac gacgcccttc acatgcaggc cctgccccct    1500
cgctaa                                                               1506

SEQ ID NO: 40          moltype =    length =
SEQUENCE: 40
000

SEQ ID NO: 41          moltype = AA   length = 6
FEATURE                Location/Qualifiers
```

```
source                 1..6
                       mol_type = protein
                       organism = synthetic construct
SEQUENCE: 41
SSGGNT                                                              6

SEQ ID NO: 42          moltype = AA  length = 15
FEATURE                Location/Qualifiers
source                 1..15
                       mol_type = protein
                       organism = synthetic construct
SEQUENCE: 42
DSYYFGNSVY YAMDY                                                   15

SEQ ID NO: 43          moltype = AA  length = 6
FEATURE                Location/Qualifiers
source                 1..6
                       mol_type = protein
                       organism = synthetic construct
SEQUENCE: 43
QDINSY                                                              6

SEQ ID NO: 44          moltype =     length =
SEQUENCE: 44
000

SEQ ID NO: 45          moltype = AA  length = 9
FEATURE                Location/Qualifiers
source                 1..9
                       mol_type = protein
                       organism = synthetic construct
SEQUENCE: 45
LQYDEFPYT                                                           9

SEQ ID NO: 46          moltype = AA  length = 15
FEATURE                Location/Qualifiers
source                 1..15
                       mol_type = protein
                       organism = synthetic construct
SEQUENCE: 46
GGGGSGGGGS GGGGS                                                   15
```

ANTI-ROR1 ANTIBODY AND ROR1-TARGETING ENGINEERED CELLS

CROSS-REFERENCE TO RELATED APPLICATIONS

This application claims priority to the U.S. Provisional application Ser. No. 63/365,230 filed on May 24, 2022, incorporated herein by reference.

STATEMENT REGARDING FEDERALLY SPONSORED RESEARCH

None.

SEQUENCE LISTING

The instant application contains a sequence listing which has been submitted electronically in XML format and is hereby incorporated by reference in its entirety. Said XML copy, created on May 22, 2023, is named CBI047.30_SL.xml and is 55,553 bytes in size.

FIELD OF THE INVENTION

The present invention relates to the field of immunology and more specifically, to antibodies, T-cell receptors, and immune cells targeting ROR1, which are useful in the field of adoptive cellular immunotherapy for tumors.

BACKGROUND OF THE INVENTION

Immunotherapy is emerging as a highly promising approach for the treatment of cancer. T cells or T lymphocytes, the armed forces of our immune system, constantly look for foreign antigens and discriminate abnormal (cancer or infected cells) from normal cells. Genetically modifying T cells or natural killer (NK) cells with CAR (chimeric antigen receptor) constructs is the most common approach to design tumor-specific T cells and NK cells. CAR-T cells and CAR-NK cells targeting tumor-associated antigens (TAA) can be infused into patients (called adoptive cell transfer or ACT) representing an efficient immunotherapy approach, see Grupp, et al., (2013) Chimeric antigen receptor-modified T cells for acute lymphoid leukemia. N Engl J Med 368, 1509-1518, and Maus, et al., (2013). T cells expressing chimeric antigen receptors can cause anaphylaxis in humans. Cancer Immunol Res 1, 26-31. The advantage of CAR-T (and CAR-NK) technology compared with chemotherapy or antibody is that engineered cells can proliferate and persist in the patient as a "living drug." Maus, et al., (2014). Antibody-modified T cells: CARs take the front seat for hematologic malignancies. Blood 123, 2625-2635, and Goluboskaya et al., (2016) Different Subsets of T Cells, Memory, Effector Functions, and CAR-T Immunotherapy. Cancers (Basel). 2016 Mar. 15; 8(3). pii: E36.

CARs usually consist of, in the N-C orientation, a monoclonal antibody-derived single-chain variable fragment (scFv), a hinge, a transmembrane domain, and one or more intracellular co-activation domains: e.g., CD8, CD28, CD137 (4-1BB), CD27; and one or more activation domains, e.g., CD3-zeta domain, see FIG. 1 and Maus (2013) and Maus (2014) supra. The evolution of CARs went from first generation (with no costimulatory domains) to second generation (with one co-stimulation domain) to third generation CAR (with several costimulatory domains). CAR-T cells with 3$^{rd}$ generation CARs having multiple costimulatory domains possess increased cytolytic activity, and improved persistence resulting in augmented antitumor activity.

Natural killer cells (NK) cells are a type of cytotoxic lymphocyte critical to the innate immune system. The role NK cells play is analogous to that of cytotoxic T cells in the vertebrate adaptive immune response. NK cells provide rapid responses to virus-infected cells, acting at around 3 days after infection, and respond to tumor formation.

Tyrosine-protein kinase transmembrane receptor ROR1, also known as neurotrophic tyrosine kinase, receptor-related 1 (NTRKR1), is an enzyme that in humans is encoded by the ROR1 gene. ROR1 is a member of the receptor tyrosine kinase-like orphan receptor (ROR) family. ROR1 is 937 amino-acid protein, with amino acids 30-406 comprising the extracellular domain. The ROR1 gene encodes a receptor tyrosine kinase-like orphan receptor that modulates neurite growth in the central nervous system. ROR1 is a glycosylated type I membrane protein that belongs to the ROR subfamily of cell surface receptors. ROR1 is the receptor for ligand WNT5A which activates downstream NF kappa B signaling pathway and may result in the inhibition of WNT-mediated signaling. In addition, ROR1 has recently been shown to be expressed on ovarian cancer stem cells and promote migration, invasion and cancer stem cell spheroid formation. ROR1 is shown to be overexpressed in both hematological cancers and solid tumors that makes it a useful target for CAR-T therapy.

Low expression of ROR1 has been shown in most of normal human tissues such as adipose and soft tissue, bone marrow and immune system, endocrine tissues, female tissue, gastrointestinal tract, kidney and urinary bladder, liver and gallbladder, lung, muscle, male tissues, and skin.

SUMMARY OF THE INVENTION

In some embodiments, the invention is anti-human ROR1 antibody or an antigen-binding fragment thereof comprising $V_H$ having an amino acid sequence at least 90% identical to SEQ ID NO: 2 and $V_L$ having an amino acid sequence at least 90% identical to SEQ ID NO: 3. In some embodiments, the anti-human ROR1 antibody or an antigen-binding fragment thereof comprises a humanized mouse amino acid sequence. In some embodiments, the antigen-binding fragment is a single-chain variable fragment (scFv). In some embodiments, the scFv comprises a $V_H$ comprising SEQ ID NO: 17, a $V_L$ comprising SEQ ID NO: 18, and a linker. In some embodiments, the scFv has a $V_H$ consisting of SEQ ID NO: 17, a $V_L$ consisting of SEQ ID NO: 18, and a linker. In some embodiments, the scFv is encoded by a nucleic acid comprising SEQ ID NO: 38. In some embodiments, the scFv comprises complementarity determining regions (CDRs) in the $V_H$ and the $V_L$, wherein a CDR1 of the $V_H$ comprises the sequence TYA, a CDR2 of the $V_H$ comprises SEQ ID NO: 41, a CDR3 of the $V_H$ comprises SEQ ID NO: 42, a CDR1 of the $V_L$ comprises SEQ ID NO: 43, a CDR2 of the $V_L$ comprises the sequence RAN, and a CDR3 of the $V_L$ comprises SEQ ID NO: 45.

In some embodiments, the invention is a chimeric antigen receptor (CAR) comprising the scFv and further comprising: a transmembrane domain, at least one co-stimulatory domains, and an activation domain. In some embodiments, the co-stimulatory domain is CD28 or 4-1BB. In some embodiments, the activation domain is CD3 zeta. In some embodiments, the transmembrane domain is a CD8 transmembrane domain. In some embodiments, the CAR further comprises a signaling peptide and a hinge domain. In some embodiments, the signaling peptide and the hinge domain are the CD8 signaling peptide and the CD8 hinge domain. In some embodiments, the CAR comprises the amino acid sequence of SEQ ID NO: 19. In some embodiments, the CAR consists of the amino acid sequence of SEQ ID NO: 19. In some embodiments, the CAR is encoded by a nucleic acid comprising sequence of SEQ ID NO: 39. In some embodiments, the invention is an engineered immune cell expressing the CAR of SEQ ID NO: 19. In some embodiments, the cell is selected from a CAR-T cell and a CAR-NK (natural killer) cell.

In some embodiments, the invention is a composition comprising the engineered immune expressing the CAR of SEQ ID NO: 19 and an excipient.

DETAILED DESCRIPTION OF THE INVENTION

Definitions

Figure 1:
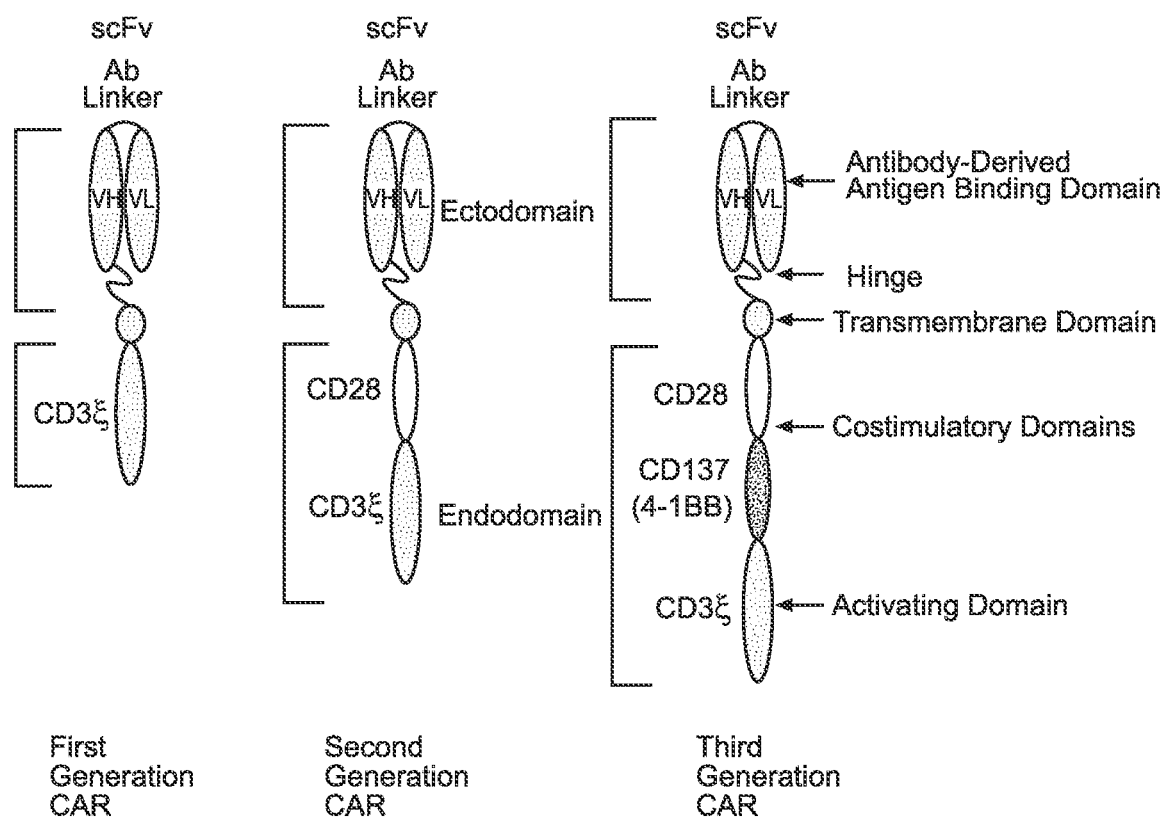
FIG. 1 is a diagram showing the first, second, and third generation chimeric antigen receptors (CARs) known in the art.

As used herein, an "antibody" refers to antigen binding proteins of the immune system. A naturally occurring antibody is a glycoprotein comprising at least two heavy (H) chains and two light (L) chains inter-connected by disulfide bonds. Each heavy chain is comprised of a heavy chain variable region (VH) and a heavy chain constant (CH) region. The heavy chain constant region is comprised of three domains, CH1, CH2 and CH3. Each light chain is comprised of a light chain variable region (VL) and a light chain constant CL region. The light chain constant region is comprised of one domain, CL. The VH and VL comprise complementarity determining regions (CDR), interspersed with regions that are more conserved, termed framework regions (FR). Each VH and VL comprises three CDRs and four FRs arranged from amino-terminus to carboxy-terminus in the following order: FR1, CDR1, FR2, CDR2, FR3, CDR3, FR4.

The term "human antibody", as used herein, is intended to include antibodies having variable regions in which both the framework and CDR regions are derived from human gene sequences. Furthermore, if the antibody contains a constant region, the constant region also is derived from human immunoglobulin sequences.

The term "humanized antibody" refers to antibodies in which CDR sequences derived from the germline of another mammalian species, such as a mouse, have been grafted onto human framework sequences. Additional framework region modifications may be made within the human framework sequences.

As used herein, an "antigen-binding fragment" refers to a protein fragment including Fab fragment, Fab' fragment, F(ab')2 fragment, and scFv with antigen-binding activity.

As used herein, a "chimeric antigen receptor (CAR)" is a receptor protein that has been engineered to give T cells a new ability to target a specific protein. The receptor is chimeric because it combines both antigen-binding and T-cell activating functions in a single receptor. CAR is a fusion protein comprising an extracellular antigen-binding domain, a transmembrane domain, and at least one intracellular domain.

As used herein, the "extracellular domain capable of binding to an antigen" means any oligopeptide or polypeptide that can bind to a certain antigen. The "intracellular domain" means any oligopeptide or polypeptide known to function as a domain that transmits a signal to cause activation or inhibition of a biological process in a cell.

As used herein, a "domain" means one region in a polypeptide which is folded into a particular structure independently of other regions.

As used herein, a "single chain variable fragment (scFv)" means a single chain polypeptide derived from an antibody which retains the ability to bind to an antigen. A typical example of an scFv includes an antigen-binding polypeptide which is formed by a recombinant DNA technique and in which Fv regions of immunoglobulin heavy chain (H chain) and light chain (L chain) fragments are linked via a spacer or linker sequence. Various methods for engineering an scFv are known to a person skilled in the art.

As used herein, a "tumor antigen" means a biological molecule having antigenicity, which is a characteristic of a tumor.

The inventors have generated an anti-ROR1 monoclonal antibody that specifically targets the human ROR1 antigen using hybridoma technology. The inventors have produced anti-ROR1 CAR-T cells to target cancer cells overexpressing the ROR1 tumor antigen. The anti-ROR1 CAR-T cells of the present invention have high cytotoxic activity against several cancer cell lines and anti-tumor activity in vivo. Anti-ROR1 CAR-NK cells expressing the same CAR are also contemplated.

In some embodiments, the present invention comprises a monoclonal mouse anti-human ROR1 antibody having the amino acid sequence of SEQ ID NO: 1, or an antigen-binding fragment thereof, comprising a $V_H$ having the amino acid sequence of SEQ ID NO: 2 and a $V_L$ having the amino acid sequence of SEQ ID NO: 3.

In some embodiments, the present invention comprises a monoclonal mouse anti-human ROR1 antibody or an antigen-binding fragment thereof, comprising a $V_H$ having the amino acid sequence of SEQ ID NO: 5 and a $V_L$ having the amino acid sequence of SEQ ID NO: 6.

In some embodiments, the present invention comprises a monoclonal humanized anti-human ROR1 antibody or an antigen-binding fragment thereof, comprising a $V_H$ having the amino acid sequence of SEQ ID NO: 9 and a $V_L$ having the amino acid sequence of SEQ ID NO: 10.

In some embodiments, the present invention comprises a monoclonal humanized anti-human ROR1 antibody or an antigen-binding fragment thereof, comprising a $V_H$ having the amino acid sequence of SEQ ID NO: 13 and a $V_L$ having the amino acid sequence of SEQ ID NO: 14.

In some embodiments, the present invention comprises a monoclonal humanized anti-human ROR1 antibody or an antigen-binding fragment thereof, comprising a $V_H$ having the amino acid sequence of SEQ ID NO: 17 and a $V_L$ having the amino acid sequence of SEQ ID NO: 18.

In some embodiments, the monoclonal anti-human ROR1 antibody is generated against the extracellular region of the purified recombinant fragment of human ROR1.

In some embodiments, the invention comprises single-chain variable fragments (scFv) derived from the monoclonal mouse anti-human ROR1 antibody disclosed herein or any of the humanized versions thereof also disclosed herein.

In some embodiments, the invention comprises a chimeric antigen receptor (CAR) fusion protein comprising from N-terminus to C-terminus: (i) a single-chain variable fragment (scFv) against ROR1 disclosed herein, (ii) a transmembrane domain, (iii) at least one co-stimulatory domain, and (iv) an activating domain.

FIG. 1 illustrates the structure of a first-generation CAR lacking the costimulatory domains, the second-generation CAR with one co-stimulatory domain (CD28 or 4-1BB), and the third-generation CAR having two or more co-stimulatory domains (adapted from Goluboskaya et al., (2016) Different Subsets of T Cells, Memory, Effector Functions, and CAR-T Immunotherapy. Cancers (Basel). 2016 Mar. 15; 8(3). pii: E36).

Figure 2:
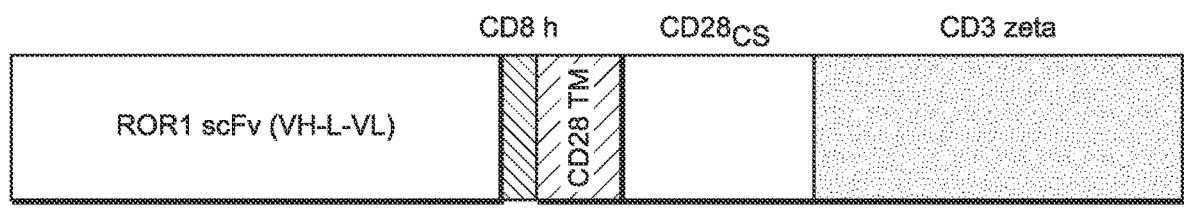
FIG. 2 is a diagram showing the structure of the anti-ROR1 CAR.

FIG. 2 illustrates the structure of the anti-ROR1 CAR of the present invention. The second-generation CAR was used with either the CD28 or the 4-1BB co-stimulatory domain. (A CAR with the CD28 co-stimulatory domain is shown.) In FIG. 2, "scFv" is a single chain variable fragment; "CD8 h" is a CD8 hinge; "CD28 TM" is a CD28 transmembrane domain; "CD28 cs" is a CD-28 co-stimulatory domain, "CD3-zeta" is a CD3 zeta activation domain, "$V_H$" is a heavy chain variable region, "L" is a linker and "$V_L$" is a light chain variable region. The arrangement of the scFv is shown as $V_H$-linker-$V_L$. In some embodiments, the arrangement is $V_L$-linker-$V_H$.

The co-stimulatory domain can be selected from the group consisting of CD28, 4-1BB (CD137), GITR, ICOS-1, CD27, OX-40 and DAP10 co-stimulatory domains. In some embodiments, the co-stimulatory domain is CD28.

In some embodiments, the activating domain is CD3 zeta (CD3 Z or CD3-zeta, encoded by the CD247 gene.

The transmembrane domain may be derived from a natural polypeptide or may be artificially designed. The transmembrane domain derived from a natural polypeptide can be obtained from any membrane-binding or transmembrane protein. In some embodiments, the transmembrane domain is a transmembrane domain of a protein selected from the group consisting of a T cell receptor α- or β-chain, a CD3-zeta chain, CD28, CD3ε, CD45, CD4, CD5, CD8, CD9, CD16, CD22, CD33, CD37, CD64, CD80, CD86, CD134, CD137, ICOS, CD154, or a GITR. The artificially designed transmembrane domain is a polypeptide mainly comprising hydrophobic residues such as leucine and valine.

In some embodiments, a triplet of phenylalanine, tryptophan and valine is found at each end of the synthetic transmembrane domain.

In some embodiments, the CAR comprises a linker between the transmembrane domain and the intracellular domain. In some embodiments, the linker is an oligopeptide or a polypeptide, for example, has a length of 2 to 10 amino acids. A peptide linker generally comprises from about 5 to about 40 amino acids. The linker can be a naturally occurring sequence or an engineered sequence. For example, in some embodiments, the linker is derived from a human protein, e.g., an immunoglobulin selected from IgG, IgA, IgD, IgE, or IgM. In some embodiments, the linker comprises 5-40 amino acids from the CH1, CH2, or CH3 domain of an immunoglobulin heavy chain. In some embodiments, the linker is a glycine and serine rich linker having the sequence $(G_xS_y)_n$. Additional linker examples and sequences are disclosed in the U.S. Pat. No. 5,525,491 Serine-rich peptide linkers, U.S. Pat. No. 5,482,858 Polypeptide linkers for production of biosynthetic proteins, and a publication WO2014087010 Improved polypeptides directed against IgE.

In some embodiments, the invention comprises one or more nucleic acids encoding the anti-ROR1 CARs. The nucleic acid encoding the CAR can be prepared from an amino-acid sequence of the specified CAR by a conventional method. A nucleotide sequence encoding an amino acid sequence can be obtained using the tools provided to the public by the National Center for Biotechnology Information (NCBI), e.g., from NCBI RefSeq IDs or accession numbers of GenBank for an amino acid sequence of each domain. The nucleic acid of the present invention can be prepared using a standard molecular biological or chemical procedure. In some embodiments, based on the nucleotide sequence, portions of the nucleic acid are synthesized. In some embodiments, the nucleic acid of the present invention is prepared by combining DNA fragments which are obtained from a cDNA library using the polymerase chain reaction (PCR).

In some embodiments, a nucleic acid encoding the CAR of the present invention is inserted into a vector, and the vector is introduced into a cell. In some embodiments, the vector is a viral vector such as a retroviral vector (including an oncoretroviral vector, a lentiviral vector, and a pseudo-type vector), an adenoviral vector, an adeno-associated virus (AAV) vector, a simian virus vector, a vaccinia virus vector, a Sendai virus vector, an Epstein-Barr virus (EBV) vector, or a herpes simplex virus (HSV) vector. In some embodiments, a viral vector lacking the replicating ability so as not to self-replicate in an infected cell is used.

In some embodiments, retroviral particles are prepared using a packaging cell line. In such embodiments, a suitable packaging cell line based on the LTR sequence, and the packaging signal sequence possessed by the viral vector is selected. Examples of the packaging cell lines include PG13 (ATCC CRL-10686), PA317 (ATCC CRL-9078), GP+E-86, GP+envAm-12, and Psi-CRIP. In some embodiments, retroviral particles are prepared using the HEK293 cell line or the HEK293t cell line having high transfection efficiency. One of skill in the art is aware of many kinds of retroviral vectors and packaging cell lines that are commercially available.

A CAR-T cell (or a CAR-NK cell) binds to a specific antigen via the CAR, whereby a signal is transmitted into the cell, and the cell is activated. The activation of the cell expressing the CAR is varied depending on the kind of the cell type and the intracellular domain of the CAR. Activation of the cell can be confirmed based on, for example, release of a cytokine, any improvement of a cell proliferation rate, a change in any cell-surface molecule, or the like. Furthermore, the release of cytotoxic cytokines (IFNγ, TNFα, etc.) from the activated CAR-T cell (or CAR-NK cell) causes destruction of a target cell expressing an antigen which can be detected or measured. In addition, release of a cytokine or change in a cell-surface molecule results in detectable or measurable stimulation of other immune cells, for example, B cells, dendritic cells, NK cells, and macrophages.

In some embodiments, the cell expressing the CAR is used as a therapeutic agent for a disease. The therapeutic agent comprises the cell expressing the CAR as an active ingredient, and it may further comprise a suitable excipient.

In one embodiment, the invention comprises anti-ROR1 scFv-CD28-CD3 zeta-CAR-T (anti-ROR1 CAR-T) cells or anti-ROR1 CAR-NK cells against cancer cells overexpressing ROR1. Anti-ROR1-CAR-T cells or CAR-NK cells express higher cytotoxic activity against ROR1-positive cancer cells compared to non-transduced (no CAR) T cells (or no CAR NK cells) and mock CAR-T cells (or mock CAR-NK cells). The mouse monoclonal anti-human ROR1 antibody disclosed herein detects ROR1 in ROR1-positive cancer cells.

In some embodiments, the invention comprises humanized $V_H$ and $V_L$ of the mouse monoclonal anti-human ROR1 antibody, a humanized scFv comprising the humanized $V_H$ and $V_L$, and CAR-T cells (or CAR-NK cells) harboring a CAR comprising the humanized anti-ROR1 scFv targeting ROR1-positive cells. Without being bound by one particular theory, the inventors perceive at least one advantage of humanizing the mouse anti-ROR1 scFv is potentially reduced immune response to the CAR-T (CAR-NK) cells in humans.

In some embodiments, the anti-ROR1 antibody or antigen binding fragment or derivative thereof (such as an scFv) comprises complementarity determining regions (CDRs). Each of the light chain and the heavy chain of an antibody comprises three CDRs. In some embodiments, CDRs are identified using crystal structure of an antigen-antibody complex. In some embodiments, CDRs are identified using in vitro methods such as phage display. In some embodiments, CDRs are identified using in silico methods, for example, IMGT (Lefranc et al., (2009) IMGT®, The international immunogenetics information system, Nucl. Acids Res. 37:D1006), and Kabat (Kabat et al., (1987) Sequences of Proteins of Immunological Interest, 4th ed., U.S. H.H.S., N.I.H.). In some embodiments, the CDRs are identified using the IMGT tool. In some embodiments, the CDRs are identified using the Kabat tool. In some embodiments, the minimal portions of the CDRs are identified as an overlap of the sequences identified by the IMGT tool and the sequences identified by the Kabat tool.

In some embodiments, the anti-ROR1 scFv comprises the sequence TYA in the CDR1 of the $V_H$. In some embodiments, the anti-ROR1 scFv comprises SEQ ID NO: 41 in the CDR2 of the $V_H$. In some embodiments, the anti-ROR1 scFv comprises SEQ ID NO: 42 in the CDR3 of the $V_H$. In some embodiments, the anti-ROR1 scFv comprises SEQ ID NO: 43 in the CDR1 of the $V_L$. In some embodiments, the anti-ROR1 scFv comprises the sequence RAN in the CDR2 of the $V_L$. In some embodiments, the anti-ROR1 scFv comprises SEQ ID NO: 45 in the CDR3 of the $V_L$.

In some the anti-ROR1 scFv anti-ROR1 comprises the sequence TYA in the CDR1 of the $V_H$, and SEQ ID NO: 41 in the CDR2 of the $V_H$, and SEQ ID NO: 42 in the CDR3 of the $V_H$ and further comprises SEQ ID NO: 43 in the CDR1 of the $V_L$, and the sequence RAN in the CDR2 of the $V_L$, and SEQ ID NO: 45 in the CDR3 of the $V_L$.

```
CDR1 heavy chain
TYA

CDR2 heavy chain
                              SEQ ID NO: 41
SSGGNT

CDR3 heavy chain
                              SEQ ID NO: 42
DSYYFGNSVYYAMDY

CDR1 light chain
                              SEQ ID NO: 43
QDINSY

CDR2 light chain
RAN

SEQ ID NO: 45
CDR3 light chain
LQYDEFPYT
```

In some embodiments, the anti-ROR1 scFv comprises complementarity determining regions CDR1, CDR2, and CDR3 in the light chain ($V_L$), and CDR1, CDR2, and CDR3 in the heavy chain ($V_H$) and comprises: the sequence TYA in the CDR1 of the $V_H$, SEQ ID NO: 41 in the CDR2 of the $V_H$, SEQ ID NO: 42 in the CDR3 of the $V_H$, SEQ ID NO: 43 in the CDR1 of the $V_L$, the sequence RAN in the CDR2 of the $V_L$, and SEQ ID NO: 45 in the CDR3 of the $V_L$. In some embodiments, in the anti-ROR1 scFv, the CDR1 of the $V_H$ consists of the sequence TYA, the CDR2 of the $V_H$ consists of SEQ ID NO: 41, the CDR3 of the $V_H$ consists of SEQ ID NO: 42, the CDR1 of the $V_L$ consists of SEQ ID NO: 43, the CDR2 of the $V_L$ consists of the sequence RAN, and the CDR3 of the $V_L$ consists of SEQ ID NO: 45.

The humanized anti-ROR1 antibody and the scFv derived therefrom that are disclosed herein can be used for immunotherapy applications: toxin-drug conjugated antibody, monoclonal therapeutic antibody, bispecific antibody, and CAR-T cell (or CAR-NK cell) based immunotherapy.

The anti-ROR1 CAR-T cells (or CAR-NIK cells) generated using the anti-ROR1 antibody disclosed herein can be effectively used to target the ROR1 antigen in ROR1-positive cells and tumors. The anti-ROR1CAR-T cells (or CAR-NIK cells) can be used clinically against tumor cells, tumors, and cancer stem cells that are resistant to chemotherapy and form aggressive tumors.

The anti-ROR1 CAR-T cells (or CAR-NK cells) can be used in combination with different therapeutic agents: checkpoint inhibitors; targeted therapies, small molecule inhibitors, antibodies and the like. For example, anti-ROR1 CAR-T cells (or CAR-NK cells) can be used in combination with CAR-T (or CAR-NK) cells targeting other tumor antigens or antigens present in the tumor microenvironment (e.g., VEGFR-1-3, PDL-1, CD80). Bi-specific antibodies and scFvs (e.g., bi-specific against ROR1 and CD3), and cells expressing the antibodies and the scFvs can be used to enhance activity of ROR1-targeting therapy.

The anti-ROR1 antibody and its derivatives disclosed herein can be modified with site-directed mutagenesis, e.g., with error-prone PCR for affinity tuning and selected by affinity maturation. Modifications of co-activation domains: CD28, 4-1BB and others can be used to increase the efficacy of the CAR generated from the antibody (and its derivatives) disclosed herein. Tag-conjugated anti-ROR1 scFv can be used for CAR generation. First, second and third generation CAR constructs can be made with the same anti-ROR1 scFv disclosed herein.

The anti-ROR1 CAR disclosed herein can be used for generating CAR-T cells, CAR-NK cells and other types of cells such as iPSCs (induced pluripotency stem cells) from which T cells, NK cells, macrophages and other anti-ROR1 CAR-expressing hematopoietic cells, which can target ROR1-positive cancers. The present invention provides T cells, or NK cells, or macrophages, or hematopoietic cells, modified to express the anti-ROR1 CAR.

The CAR-expressing cells disclosed herein can be autologous cells and allogenic cells.

The following examples further illustrate the present invention. These examples are intended merely to be illustrative of the present invention and are not to be construed as being limiting.

EXAMPLES

The inventors generated anti-ROR1 CAR constructs and cloned the constructs into lentiviral vectors. The CAR construct contains the anti-ROR1 ScFv-CD28-CD3zeta insert (or similar insert with 41BB co-stimulatory domain instead of CD28 domain). CMV, EF1 or MNDU3 promoter can be used to drive expression of CAR construct. The lentiviruses were generated in HEK293t cells and titer was established by RT-PCR. Then equal dose of lentiviruses was used for transduction of T cells, as described in Examples.

Figure 3:
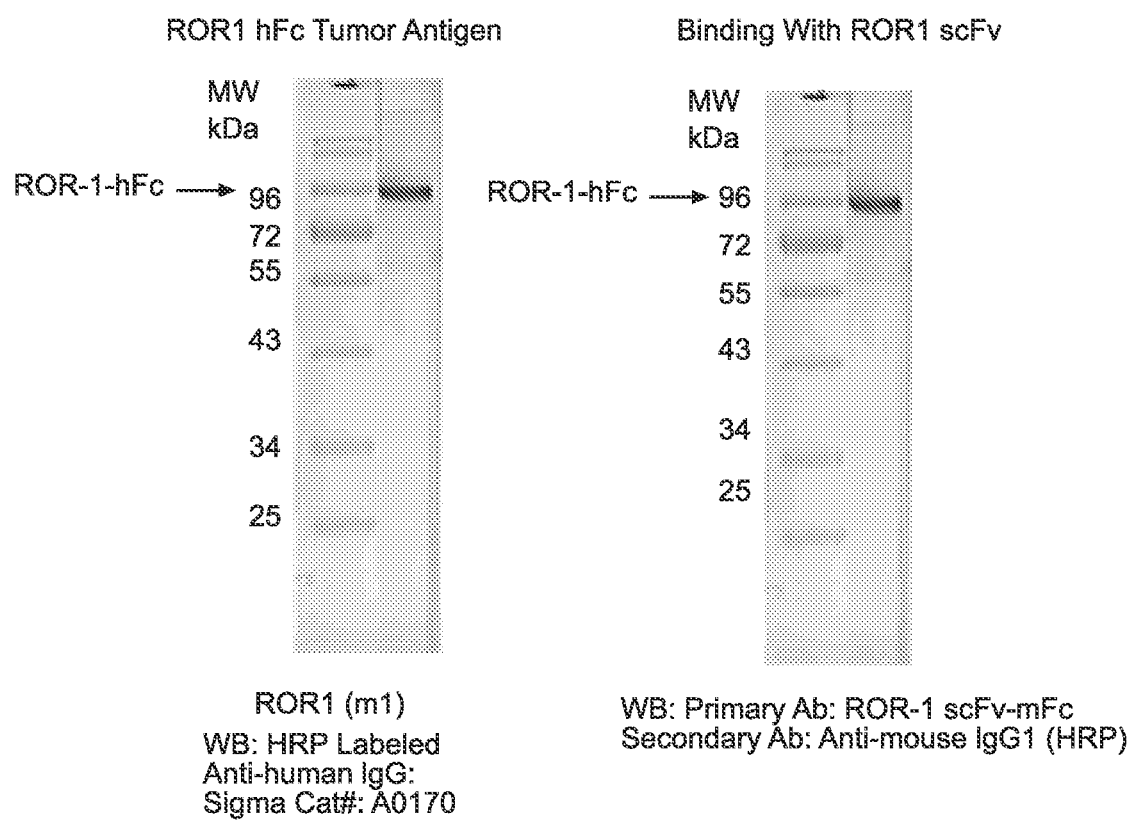
FIG. 3 is a Western blot demonstrating binding of the anti-ROR1 antibody to human ROR1 antigen.

Example 1. Anti-ROR1 scFv Detected the ROR1 Protein by Western Blotting, and the Anti-ROR1 Antibody Detected ROR1 by FACS Staining In this example, we generated a mouse monoclonal anti-ROR1 antibody using standard hybridoma technology. The mouse anti-ROR1 antibody (IgG1 type) detected extracellular ROR1 protein by ELISA (data not shown). We sequenced this hybridoma clone 2H6 and generated an scFv using $V_H$ and $V_L$ (see further in Example 2). We performed a Western blot demonstrating that the anti-ROR1 scFv bound ROR1 extracellular domain fused to human Fc (hFc) protein (FIG. 3, left panel). The ROR1-human Fc fusion protein was detected with an antibody directed against the human Fc domain. FIG. 3, right panel shows ROR1 antigen detected with the anti-ROR1 scFv-mouse Fc fusion as a primary antibody and anti-mouse IgG-HRP as a secondary antibody.

Figure 4:
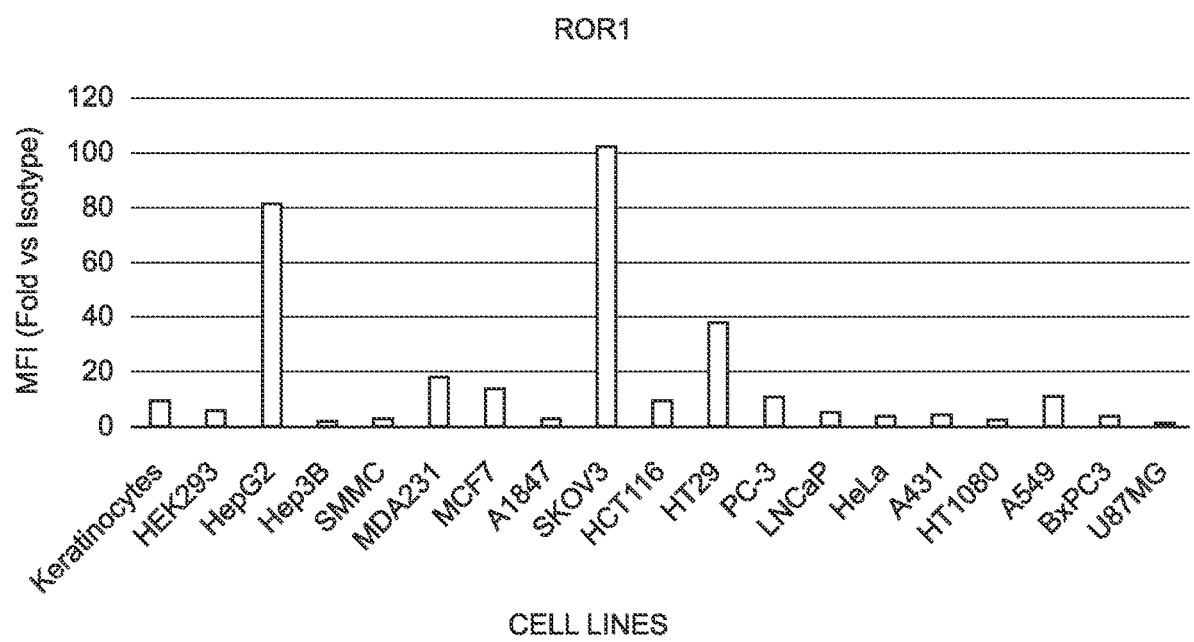
FIG. 4 shows FACS data demonstrating staining of different cell lines with the anti-ROR1 antibody using different cancer cell lines.

We further performed a fluorescence activated cell sorting (FACS) experiment demonstrating that the mouse anti-ROR1 monoclonal antibody detected elevated expression of ROR1 in several cancer cell lines such as hepatocellular carcinoma (HepG2), breast cancer (MDA231), colon cancer (HT-29), and ovarian cancer (SKOV-3). Normal keratinocytes were used as a negative control (FIG. 4). (MFI: medium fluorescence intensity compared to the isotype).

Example 2. Sequencing of Anti-ROR1 $V_H$, $V_L$, and CAR Constructs

In this example we sequenced the anti-ROR1 antibody, hybridoma clone 2H6. The sequences of $V_H$, $V_L$, and the scFv are shown below. The structure of the anti-ROR1 scFv is: $V_H$-linker-$V_L$ with the linker having the sequence (G4S)3 (SEQ ID NO: 46). In the sequences below the sequence starts with the $V_H$; the underline shows the nucleotide sequence of $V_L$; the linker sequence is in italics.

Anti-ROR1 scFv (mouse clone 2H6)
nucleotide sequence (SEQ ID NO: 20):
GTGAAGCTGGTGGAGTCTGGGGGAGGCTTAGTGAAGCCTGGAGGG

TCCCTGAAACTCTCCTGTGCAGCCTCTGGATTCACTTTCAGTACC

TATGCCATGTCTTGGGTTCGCCAGACTCCAGAGAAGAGGCTGGAG

TGGGTCGCATCCATTAGTAGTGGTGGTAACACCTACTATCCAGAC

AGTGTGAAGGGCCGATTCACCATCTCCAGAGATAATGCCAGGCAC

ATCCTGTACCTGCAAATGAGCAGTCTGAGGTCTGAGGACACGGCC

ATGTATTACTGTGCAAGAGATTCTTATTACTTCGGTAATAGCGTT

TACTATGCTATGGACTACTGGGGTCAAGGAACCTCAGTCACCGTC

TCCTCA*GGTGGCGGTGGTTCTGGTGGCGGTGGTTCTGGTGGCGGT*

*GGTTCT*GACATCAAGATGACCCAGTCTCCATCTTCCATGTATGCA

TCTCTAGGAGAGAGTCACTATCACTTGCAAGGCGAGTCAGGAC

ATTAATAGCTATTTTAGCTGGTTCCAGCAAAAACCAGGGAAATCT

CCTAAGACCCTGATCTATCGTGCAAATAGATTGGTAGATGGGGTC

CCATCAAGGTTCAGTGGCAGTGGATCTGGGCAGGATTATTCTCTC

ACCATCAGCAGCCTGGAGTATGAAGATATGGGAATTTATTATTGT

CTACAGTATGATGAGTTTCCGTACACGTTCGGAGGGGGGACCAAA

CTGGAAATAAAACGG

Anti-ROR1 scFv (mouse clone 2H6)
amino acid sequence: (SEQ ID NO: 1):
VKLVESGGGLVKPGGSLKLSCAASGFTFSTYAMSWVRQTPEKRLE

WVASISSGGNTYYPDSVKGRFTISRDNARHILYLQMSSLRSEDTA

MYYCARDSYYFGNSVYYAMDYWGQGTSVTVSS*GGGGSGGGGSGGG*

*GS*DIKMTQSPSSMYASLGERVTITCKASQDINSYFSWFQQKPGKS

PKTLIYRANRLVDGVPSRFSGSGSGQDYSLTISSLEYEDMGIYYC

LQYDEFPYTFGGGTKLEIKR

Anti-ROR1 scFv (mouse clone 2H6) $V_H$
amino acid sequence (SEQ ID NO: 2):
VKLVESGGGLVKPGGSLKLSCAASGFTFSTYAMSWVRQTPEKRLE

WVASISSGGNTYYPDSVKGRFTISRDNARHILYLQMSSLRSEDTA

MYYCARDSYYFGNSVYYAMDYWGQGTSVTVSS

Anti-ROR1 scFv (mouse clone 2H6) $V_L$
amino acid sequence (SEQ ID NO: 3):
DIKMTQSPSSMYASLGERVTITCKASQDINSYFSWFQQKPGKSPK

TLIYRANRLVDGVPSRFSGSGSGQDYSLTISSLEYEDMGIYYCLQ

YDEFPYTFGGGTKLEIKR

Example 3. Anti-ROR1-CAR Sequences with Mouse Anti-ROR1 scFv

In this example we designed a CAR with the scFv derived from the mouse anti-ROR1 antibody 2H6. The scheme of the anti-ROR1 CAR construct is shown in FIG. 2. The lentiviral vector lenti CMV-MCS-EF1a-puro was used for cloning of the CAR sequence. The CD3 zeta CAR construct was under the control of the CMV promoter. For 4-1BB CAR construct we used another lentiviral vector with MNDU3 promoter to get higher percent of CAR expressing cells.

A. CD28 as a Co-stimulating Domain

The CAR comprises the following structure: anti-ROR1 ScFv-CD8 hinge—CD28 TM-CD28 co-stimulatory domains CD3 zeta activation domain (FIG. 2). The structure further includes the human CD8 signaling peptide. The anti-ROR1 scFv has the structure $V_H$-Linker $(G_4S)_3$—$V_L$ ("$(G_4S)_3$" disclosed as SEQ ID NO: 46).

```
CD8 signaling peptide nucleotide sequence
(SEQ ID NO: 21):
ATGGCCTTACCAGTGACCGCCTTGCTCCTGCCGCTGGCCT

TGCTGCTCCACGCCGCCAGGCCG

CD8 signaling peptide amino-acid sequence
(SEQ ID NO: 22):
MALPVTALLLPLALLLHAARP Nhe I restriction site: GCTAGC XhoI restriction site: CTCGAG CD8 hinge nucleotide sequence
(SEQ ID NO: 24):
AAGCCCACCACGACGCCAGCGCCGCGACCACCAACACCGG

CGCCCACCATCGCGTCGCAGCCCCTGTCCCTGCGCCCAGA

GGCGAGCCGGCCAGCGCGCGGGGGGGCAGTGCACACGAGG

GGGCTGGACTTCGCCAGTGAT

CD8 hinge amino acid sequence
(SEQ ID NO: 25):
KPTTTPAPRPPTPAPTIASQPLSLRPEASRPAAGGAVHTRG

LDFASD

CD28 TM/activation nucleotide sequence
(SEQ ID NO: 26):
TTTTGGGTGCTGGTGGTGGTTGGTGGAGTCCTGGCTTGCT

ATAGCTTGCTAGTAACAGTGGCCTTTATTATTTTCTGGGT

GAGGAGTAAGAGGAGCAGGCTCCTGCACAGTGACTACATG

AACATGACTCCCCGCCGCCCCGGGCCCACCCGCAAGCATT

ACCAGCCCTATGCCCCACCACGCGACTTCGCAGCCTATCG

CTCC

CD28 TM/activation amino acid sequence
(SEQ ID NO: 27):
FWVLVVVGGVLACYSLLVTVAFIIFWV/RSKRSRLLHSDY

MNMTPRRPGPTRKHYQPYAPPRDFAAYRS

CD3 zeta nucleotide sequence
(SEQ ID NO: 28):
AGAGTGAAGTTCAGCAGGAGCGCAGACGCCCCCGCGTACC

AGCAGGGCCAGAACCAGCTCTATAACGAGCTCAATCTAGG

ACGAAGAGAGGAGTACGATGTTTTGGACAAGAGACGTGGC

CGGGACCCTGAGATGGGGGGAAAGCCGCAGAGAAGGAAGA

ACCCTCAGGAAGGCCTGTACAATGAACTGCAGAAAGATAA

GATGGCGGAGGCCTACAGTGAGATTGGGATGAAAGGCGAG

CGCCGGAGGGGCAAGGGGCACGATGGCCTTTACCAGGGTC

TCAGTACAGCCACCAAGGACACCTACGACGCCCTTCACAT

GCAGGCCCTGCCCCCTCGC
```

```
CD3 zeta amino acid sequence
(SEQ ID NO: 29):
RVKFSRSADAPAYQQGQNQLYNELNLGRREEYDVLDKRRG

RDPEMGGKPQRRKNPQEGLYNELQKDKMAEAYSEIGMKGE

RRRGKGHDGLYQGLSTATKDTYDALHMQALPPR

EcoRI restriction site: GAATTC

Anti-ROR1 CAR (mouse) nucleotide sequence
(SEQ ID NO: 30):
ATGGCCTTACCAGTGACCGCCTTGCTCCTGCCGCTGGCCT

TGCTGCTCCACGCCGCCAGGCCGGCTAGCGTGAAGCTGGT

GGAGTCTGGGGGAGGCTTAGTGAAGCCTGGAGGGTCCCTG

AAACTCTCCTGTGCAGCCTCTGGATTCACTTTCAGTACCT

ATGCCATGTCTTGGGTTCGCCAGACTCCAGAGAAGAGGCT

GGAGTGGGTCGCATCCATTAGTAGTGGTGGTAACACCTAC

TATCCAGACAGTGTGAAGGGCCGATTCACCATCTCCAGAG

ATAATGCCAGGCACATCCTGTACCTGCAAATGAGCAGTCT

GAGGTCTGAGGACACGGCCATGTATTACTGTGCAAGAGAT

TCTTATTACTTCGGTAATAGCGTTTACTATGCTATGGACT

ACTGGGGTCAAGGAACCTCAGTCACCGTCTCCTCAGGTGG

CGGTGGTTCTGGTGGCGGTGGTTCTGGTGGCGGTGGTTCT

GACATCAAGATGACCCAGTCTCCATCTTCCATGTATGCAT

CTCTAGGAGAGAGTCACTATCACTTGCAAGGCGAGTCA

GGACATTAATAGCTATTTTAGCTGGTTCCAGCAAAAACCA

GGGAAATCTCCTAAGACCCTGATCTATCGTGCAAATAGAT

TGGTAGATGGGGTCCCATCAAGGTTCAGTGGCAGTGGATC

TGGGCAGGATTATTCTCTCACCATCAGCAGCCTGGAGTAT

GAAGATATGGGAATTTATTATTGTCTACAGTATGATGAGT

TTCCGTACACGTTCGGAGGGGGGACCAAACTGGAAATAAA

ACGGCTCGAGAAGCCCACCACGACGCCAGCGCCGCGACCA

CCAACACCGGCGCCCACCATCGCGTCGCAGCCCCTGTCCC

TGCGCCCAGAGGCGAGCCGGCCAGCGGCGGGGGGCGCAGT

GCACACGAGGGGCTGGACTTCGCCAGTGATAAGCCCTTT

TGGGTGCTGGTGGTGGTTGGTGGAGTCCTGGCTTGCTATA

GCTTGCTAGTAACAGTGGCCTTTATTATTTTCTGGGTGAG

GAGTAAGAGGAGCAGGCTCCTGCACAGTGACTACATGAAC

ATGACTCCCCGCCGCCCCGGGCCCACCCGCAAGCATTACC

AGCCCTATGCCCCACCACGCGACTTCGCAGCCTATCGCTC

CAGAGTGAAGTTCAGCAGGAGCGCAGACGCCCCCGCGTAC

CAGCAGGGCCAGAACCAGCTCTATAACGAGCTCAATCTAG

GACGAAGAGAGGAGTACGATGTTTTGGACAAGAGACGTGG

CCGGGACCCTGAGATGGGGGGAAAGCCGCAGAGAAGGAAG

AACCCTCAGGAAGGCCTGTACAATGAACTGCAGAAAGATA
```

```
AGATGGCGGAGGCCTACAGTGAGATTGGGATGAAAGGCGA

GCGCCGGAGGGGCAAGGGGCACGATGGCCTTTACCAGGGT

CTCAGTACAGCCACCAAGGACACCTACGACGCCCTTCACA

TGCAGGCCCTGCCCCCTCGCTAA

Anti-ROR1 CAR (mouse) amino acid sequence
(SEQ ID NO: 4):
MALPVTALLLPLALLLHAARPASVKLVESGGGLVKPGGSL

KLSCAASGFTFSTYAMSWVRQTPEKRLEWVASISSGGNTY

YPDSVKGRFTISRDNARHILYLQMSSLRSEDTAMYYCARD

SYYFGNSVYYAMDYWGQGTSVTVSSGGGGSGGGGSGGGGS

DIKMTQSPSSMYASLGERVTITCKASQDINSYFSWFQQKP

GKSPKTLIYRANRLVDGVPSRFSGSGSGQDYSLTISSLEY

EDMGIYYCLQYDEFPYTFGGGTKLEIKRLEKPTTTPAPRP
```

```
PTPAPTIASQPLSLRPEASRPAAGGAVHTRGLDFASDKPF

WVLVVVGGVLACYSLLVTVAFIIFWVRSKRSRLLHSDYMN

MTPRRPGPTRKHYQPYAPPRDFAAYRSRVKFSRSADAPAY

QQGQNQLYNELNLGRREEYDVLDKRRGRDPEMGGKPQRRK

NPQEGLYNELQKDKMAEAYSEIGMKGERRRGKGHDGLYQG

LSTATKDTYDALHMQALPPR
```

We also generated a CAR with the 4-1BB co-stimulatory domain in place of the CD28 activation domain. This construct PMC1195 was cloned in a vector with the KanR gene. The ROR1 scFv was inserted between Nhe I and Xho I sites in the sequence (underlined). The CAR expression was under the control of the MNDU3 promoter.

The nucleotide sequence of the codon-optimized CAR (anti-ROR1 scFv-4-1BB-CD3 zeta) is shown below. The scFv is inserted between Nhe I and Xho I sites (underlined). 4-1BB is in italics followed by the CD3-zeta domain.

```
(SEQ ID NO: 31):
ATGGCCTTACCAGTGACCGCCTTGCTCCTGCCGCTGGCCTTGCTGCTCC

ACGCCGCCAGGCCGGCTAGCGAAGTGAAGCTTGTCGAATCCGGCGGTGGATTGGTT

AAACCAGGCGGAAGTTTGAAACTGAGTTGTGCTGCTTCTGGTTTTACCTTTAGCACA

TACGCTATGTCCTGGGTTAGGCAGACGCCGGAGAAACGATTGGAGTGGTAGCATCT

ATTTCTTCTGGCGGCAATACTTATTACCCTGACAGCGTGAAAGGCCGGTTCACTATTT

CTCGAGATAATGCGCGGCACATACTCTATCTCCAGATGTCTTCTCTCCGCTCAGAGG

ATACAGCGATGTACTATTGTGCAAGGGATAGTTACTATTTCGGAAACTCTGTGTATT

Anti-ROR1 CAR (4-1BB in place of CD28 activation domain)
nucleotide sequence
ATGCAATGGATTACTGGGGTCAGGGAACTTCAGTCACAGTAAGCTCAGGTGGGGGA

GGAAGCGGCGGTGGCGGCTCAGGGGGAGGTGGATCTGATATTAAAATGACTCAGTC

TCCATCAAGCATGTACGCCTCTCTGGGAGAGCGAGTTACTATTACCTGTAAAGCATC

ACAAGATATTAACTCTTATTTTAGTTGGTTTCAACAAAAGCCTGGAAAATCACCTAA

AACTTTGATTTATAGAGCCAATAGGCTTGTGGATGGTGTACCTAGTCGGTTTAGCGG

CTCAGGGTCAGGCCAAGACTATTCTTTGACCATCTCTTCTCTGGAGTATGAGGACAT

GGGAATCTATTACTGTCTTCAGTACGATGAGTTCCCCTATACGTTTGGTGGAGGCAC

TAAATTGGAGATTAAACTCGAGAAGCCCACCACGACGCCAGCGCCGCGACCACCAA

CACCGGCGCCCACCATCGCGTCGCAGCCCCTGTCCCTGCGCCCAGAGGCGAGCCGG

CCAGCGGCGGGGGGCGCAGTGCACACGAGGGGGCTGGACTTCGCCAGTGATAAGCC

CTTTTGGGTGCTGGTGGTGGTTGGTGGAGTCCTGGCTTGCTATAGCTTGCTAGTAAC

AGTGGCCTTTATTATTTTCTGGGTGAAACGGGGCAGAAAGAAACTCCTGTATATATT

CAAACAACCATTTATGAGACCAGTACAAACTACTCAAGAGGAAGATGGCTGTAGCTGC

CGATTTCCAGAAGAAGAAGAAGGAGGATGTGAACTGAGAGTGAAGTTCAGCAGGAGCG

CAGACGCCCCCGCGTACCAGCAGGGCCAGAACCAGCTCTATAACGAGCTCAATCTAGG

ACGAAGAGAGGAGTACGATGTTTTGGACAAGAGACGTGGCCGGGACCCTGAGATGGG

GGGAAAGCCGCAGAGAAGGAAGAACCCTCAGGAAGGCCTCTACAATGAACTGCAGAA

AGATAAGATGGCGGAGGCCTACAGTGAGATTGGGATGAAAGGCGAGCGCCGGAGG
```

```
GGCAAGGGGCACGATGGCCTTTACCAGGGTCTCAGTACAGCCACCAAGGACACCTA
CGACGCCCTTCACATGCAGGCCCTGCCCCCTCGCTAA
```

B. 4-1BB as a Co-Stimulating Domain

We also constructed a CAR with the structure (human CD8 signaling peptide-alternative (see below) anti-ROR1 scFv (V$_H$-Linker (G$_4$S)$_3$—V$_L$ ("(G$_4$S)$_3$" disclosed as SEQ ID NO: 46)), CD8 hinge, CD28 transmembrane domain, 4-1BB co-stimulatory domain, CD3 zeta activation domain).

In the alternative scFv, each segment of the sequence is the same as that in Example 3 (A) except V$_H$, V$_L$. V$_H$ is represented by SEQ ID NO: 5 (the first amino acid was E, not present in SEQ ID NO: 2). V$_L$ is represented by SEQ ID NO: 6 (the terminal R is removed compared to SEQ ID NO: 3.

```
Alternative anti-ROR1 scFv amino acid sequence
(SEQ ID NO: 23):
EVKLVESGGGLVKPGGSLKLSCAASGFTFSTYAMSWVRQTPEKRLEWVASISS

GGNTYYPDSVKGRFTISRDNARHILYLQMSSLRSEDTAMYYCARDSYYFGNSVYYAMD

YWGQGTSVTVSSGGGGSGGGGSGGGGSDIKMTQSPSSMYASLGERVTITCKASQDINS

YFSWFQQKPGKSPKTLIYRANRLVDGVPSRFSGSGSGQDYSLTISSLEYEDMGIYYCL

QYDEFPYTFGGGTKLEIK

Anti-ROR1 CAR alternative V_H amino acid sequence
(SEQ ID NO: 5):
EVKLVESGGGLVKPGGSLKLSCAASGFTFSTYAMSWVRQTPEKRLEWVASISS

GGNTYYPDSVKGRFTISRDNARHILYLQMSSLRSEDTAMYYCARDSYYFGNSV

YYAMDYWGQGTSVTVSS
Compared with SEQ ID NO: 2, SEQ ID NO: 5 has an extra E
on the N-terminal end.

Anti-ROR1 CAR alternative V_L acid sequence
(SEQ ID NO: 6):
DIKMTQSPSSMYASLGERVTITCKASQDINSYFSWFQQKPGKSPKTLIYRANRL VDGVPSRFSGSGSGQDYSLTISSLEYEDMGIYYCLQYDEFPYTFGGGTKLEIK
Compared with SEQ ID NO: 3, SEQ ID NO: 6 is lacking the
R at the C-terminal end.

4-1BB domain nucleotide sequence:
(SEQ ID NO: 32):
AAACGGGGCAGAAGAAACTCCTGTATATATTCAAACAACCATTTATGAGA

CCAGTACAAACTACTCAAGAGGAAGATGGCTGTAGCTGCCGATTTCCAGAA

GAAGAAGAAGGAGGATGTGAACTG 4-1BB amino acid sequence
(SEQ ID NO: 33):
KRGRKKLLYIFKQPFMRPVQTTQEEDGCSCRFPEEEGGCEL Anti-ROR1 CAR (alternative scFv and 4-1BB)
amino acid sequence (SEQ ID NO: 7):
(V_H is underlined, the linker (G_4S)_3 (SEQ ID NO: 46) is in
italics, V_L is underlined; 4-1BB domain
is in underlined italics.)
MALPVTALLLPLALLLHAARPASEVKLVESGGGLVKPGGSLKLSCAASGFTFST

YAMSWVRQTPEKRLEWVASISSGGNTYYPDSVKGRFTISRDNARHILYLQMSSLRSEDT

AMYYCARDSYYFGNSVYYAMDYWGQGTSVTVSSGGGGSGGGGSGGGGSDIKMTQSPSSM

YASLGERVTITCKASQDINSYFSWFQQKPGKSPKTLIYRANRLVDGVPSRFSGSGSGQD

YSLTISSLEYEDMGIYYCLQYDEFPYTFGGGTKLEIKLEKPTTTPAPRPPTPAPTIASQ

PLSLRPEASRPAAGGAVHTRGLDFASDKPFWVLVVVGGVLACYSLLVTVAFIIFWVKRG

RKKLLYIFKOPFMRPVOTTOEEDGCSCRFPEEEEGGCELRVKFSRSADAPAYQQGQNQL

YNELNLGRREEYDVLDKRRGRDPEMGGKPQRRKNPQEGLYNELQKDKMAEAYSEIGMKG

ERRRGKGHDGLYQGLSTATKDTYDALHMQALPPR.
```

Example 4. ROR1 CAR with Humanized ROR1 scFv

In this example we humanized the mouse anti-ROR1 $V_H$ (SEQ ID NO: 5) and mouse $V_L$ (SEQ ID NO: 6) and generated several humanized scFv. We generated CARs with the three scFvs having the same structure as Example 3 (B) with the 4-1BB domain and the CD3 zeta domain. We tested several humanized scFv and selected three scFv based on best performance in functional assays shown below. The humanized scFv were inserted between Nhe I and Xho I sites in CAR sequence.

The three CARs with humanized anti-ROR1 scFv: PMC857, PMC858 and PMC862 are shown below.

```
A. PMC857 scFv and CAR
Humanized anti-ROR1 scFv PMC857 nucleotide sequence: (SEQ ID NO: 34):
GAA GTA CAG CTT GTT GAA TCA GGT GGT GGT CTT ATT CAG CCA GGA

GGC TCC TTG CGA CTG AGC TGT GCC GCT TCT GGG TTC ACC TTT AGC ACT TAC

GCA ATG AGT TGG GTC CGA CAA GCC CCA GGT AAG GGA TTG GAA TGG GTA AGT

TCC ATT TCC AGC GGA GGG AAC ACT TAT TAC GCC GAT TCT GTG AAA GGA CGC

TTT ACT ATA TCC CGA GAC AAT AGT AAA AAC ACA TTG TAT TTG CAA ATG AAC

TCT TTG AGG GCC GAG GAC ACT GCC GTC TAC TAT TGT GCC CGC GAC AGC TAT

TAT TTC GGC AAC TCT GTG TAT TAC GCG ATG GAT TAC TGG GGT GCC GGC ACA

ACT GTC ACC GTT TCA TCT GGC GGA GGA GGC AGT GGC GGA GGG GGC TCA GGC

GGT GGT GGA AGT GAT ATT CAA ATG ACC CAA TCA CCC TCT TCA TTG TCT GCA

AGC GTA GGT GAC CGA GTC ACG ATA ACC TGC AAA GCC TCT CAA GAT ATT AAT

TCA TAC TTT TCT TGG TTT CAA CAA AAA CCG GGA AAG GCG CCT AAG TCA TTG

ATT TAC CGC GCG AAC CGG TTG GTA TCA GGA GTA CCG TCA AGA TTC TCA GGG

AGT GGG TCA GGC ACA GAT TTC ACA CTC ACT ATT TCT CCT TGC AAC CCT GAA

GAC TTC GCA ACC TAT TAT GCC TTG CAG TAT GAT GAG TTT CCG TAC ACT TTC

GGG GGG GGT ACA AGG CTG GAG ATC AAA
Humanized anti-ROR1 scFv PMC857 amino acid sequence:
(SEQ ID NO: 8):
EVQLVESGGGLIQPGGSLRLSCAASGFTFSTYAMSWVRQAPGKGLEWVSSISSGG

NTYYADSVKGRFTISRDNSKNTLYLQMNSLRAEDTAVYYCARDSYYFGNSVYYAM

DYWGAGTTVTVSSGGGGSGGGGSGGGGSDIQMTQSPSSLSASVGDRVTITCKASQDINS

YFSWFQQKPGKAPKSLIYRANRLVSGVPSRFSGSGSGTDFTLTISSLQPEDFATYYCLQY

DEFPYTFGGGTRLEIK

Humanized anti-ROR1 scFv PMC857 $V_H$ amino acid sequence
(SEQ ID NO: 9):
EVQLVESGGGLIQPGGSLRLSCAASGFTFSTYAMSWVRQAPGKGLEWVSSISS

GGNTYYADSVKGRFTISRDNSKNTLYLQMNSLRAEDTAVYYCARDSYYFGNSVYYAM

DYWGAGTTVTV

Humanized anti-ROR1 scFv (PMC857) $V_L$ amino acid sequence
(SEQ ID NO: 10):
DIQMTQSPSSLSASVGDRVTITCKASQDINSYFSWFQQKPGKAPKSLIYRANRL

VSGVPSRFSGSGSGTDFTLTISSLQPEDFATYYCLQYDEFPYTFGGGTRLEIK

Humanized anti-ROR1 CAR scFv PMC857 nucleotide sequence:
(SEQ ID NO: 35):
ATGGCCTTACCAGTGACCGCCTTGCTCCTGCCGCTGGCCTTGCTGCTCCACG

CCGCCAGGCCGGCTAGC GAA GTA CAG CTT GTT GAA TCA GGT GGT GGT CTT ATT

CAG CCA GGA GGC TCC TTG CGA CTG AGC TGT GCC GCT TCT GGG TTC ACC TTT

AGC ACT TAC GCA ATG AGT TGG GTC CGA CAA GCC CCA GGT AAG GGA TTG GAA

TGG GTA AGT TCC ATT TCC AGC GGA GGG AAC ACT TAT TAC GCC GAT TCT GTG

AAA GGA CGC TTT ACT ATA TCC CGA GAC AAT AGT AAA AAC ACA TTG TAT TTG
```

CAA ATG AAC TCT TTG AGG GCC GAG GAC ACT GCC GTC TAC TAT TGT GCC CGC

GAC AGC TAT TAT TTC GGC AAC TCT GTG TAT TAC GCG ATG GAT TAC TGG GGT

GCC GGC ACA ACT GTC ACC GTT TCA TCT GGC GGA GGA GGC AGT GGC GGA GGG

GGC TCA GGC GGT GGT GGA AGT GAT ATT CAA ATG ACC CAA TCA CCC TCT TCA

TTG TCT GCA AGC GTA GGT GAC CGA GTC ACG ATA ACC TGC AAA GCC TCT CAA

GAT ATT AAT TCA TAC TTT TCT TGG TTT CAA CAA AAA CCG GGA AAG GCG CCT

AAG TCA TTG ATT TAC CGC GCG AAC CGG TTG GTA TCA GGA GTA CCG TCA AGA

TTC TCA GGG AGT GGG TCA GGC ACA GAT TTC ACA CTC ACT ATT TCT CCC TTG

CAA CCT GAA GAC TTC GCA ACC TAT TAT TGC TTG CAG TAT GAT GAG TTT CCG

TACACTTTCGGGGGGGGTACAAGGCTGGAGATCAAACTCGAGAAGCCCACCACGAC

GCCAGCGCCGCGACCACCAACACCGGCGCCCACCATCGCGTCGCAGCCCCTGTCCCT

GCGCCCAGAGGCGAGCCGGCCAGCGGCGGGGGCGCAGTGCACACGAGGGGGCTG

GACTTCGCCAGTGATAAGCCCTTTTGGGTGCTGGTGGTGGTTGGTGGAGTCCTGGCT

TGCTATAGCTTGCTAGTAACAGTGGCCTTTATTATTTTCTGGGTGAAACGGGGCAGA

AAGAAACTCCTGTATATATTCAAACAACCATTTATGAGACCAGTACAAACTACTCAA

GAGGAAGATGGCTGTAGCTGCCGATTTCCAGAAGAAGAAGAAGGAGGATGTGAACT

GAGAGTGAAGTTCAGCAGGAGCGCAGACGCCCCCGCGTACCAGCAGGGCCAGAAC

CAGCTCTATAACGAGCTCAATCTAGGACGAAGAGAGGAGTACGATGTTTTGGACAA

GAGACGTGGCCGGGACCCTGAGATGGGGGGAAAGCCGCAGAGAAGGAAGAACCCT

CAGGAAGGCCTCTACAATGAACTGCAGAAAGATAAGATGGCGGAGGCCTACAGTGA

GATTGGGATGAAAGGCGAGCGCCGGAGGGGCAAGGGGCACGATGGCCTTTACCAGG

GTCTCAGTACAGCCACCAAGGACACCTACGACGCCCTTCACATGCAGGCCCTGCCC

CCTCGCTAA

Humanized anti-ROR1 CAR (scFv PMC857) amino acid sequence:
(SEQ ID NO: 11):
MALPVTALLLPLALLLHAARPASEVQLVESGGGLIQPGGSLRLSCAASGFTFST

YAMSWVRQAPGKGLEWVSSISSGGNTYYADSVKGRFTISRDNSKNTLYLQMNSLRAED

TAVYYCARDSYYFGNSVYYAMDYWGAGTTVTVSSGGGGSGGGGSGGGGSDIQMTQSPS

SLSASVGDRVTITCKASQDINSYFSWFQQKPGKAPKSLIYRANRLVSGVPSRFSGSGSG

TDFTLTISSLQPEDFATYYCLQYDEFPYTFGGGTRLEIKLEKPTTTPAPRPPTPAPTIA

SQPLSLRPEASRPAAGGAVHTRGLDFASDKPFWVLVVVGGVLACYSLLVTVAFIIFWVK

RGRKKLLYIFKQPFMRPVQTTQEEDGCSCRFPEEEEGGCELRVKFSRSADAPAYQQGQN

QLYNELNLGRREEYDVLDKRRGRDPEMGGKPQRRKNPQEGLYNELQKDKMAEAYSEIGM

KGERRRGKGHDGLYQGLSTATKDTYDALHMQALPPR

B. PMC858 scFv and CAR
Humanized anti-ROR1 scFv PMC858 nucleotide sequence
(SEQ ID NO: 36):
CAG GTA CAA TTG GTA GAG TCC GGC GGA GGG GTT GTT

CAG CCA GGA

CGG TCC TTG CGG TTG TCT TGT GCT GCG TCA GGA TTC

ACA TTC TCA ACG TAC GCG ATG TCT TGG GTG CGC CAA

GCT CCC GGT AAA GGG CTG GAA TGG GTG GCC TCA ATC

TCA TCT GGA GGG AAC ACT TAC TAC CCT GAT AGT GTT

```
AAA GGT CGC TTT ACT ATC TCA AGG GAC AAT AGC AAG

AAT ACC TTG TAT CTG CAA ATG AAC TCA CTT AGA GCA

GAG GAC ACA GCG TAT TAC TGT GCT AGA GAC TCA

TAT TAT TTC GGC AAC TCC GTT TAT TAC GCG ATG GAT

TAC TGG GGC GCA GGG ACT ACG GTA ACT GTA TCT TCT

GGT GGT GGA GGG TCT GGG GGC GGG GGT AGT GGC GGC

GGT GGC AGT GAC ATC CAG ATG ACA CAG TCT CCG TCT

TCA TTG AGT GCA AGC GTC GGC GAT CGG GTT ACC ATT

ACG TGT AAG GCA AGT CAG GAC ATC AAC AGT TAT TTT

TCA TGG TTT CAA CAA AAG CCT GGA AAA GCG CCG AAA

TCA CTC ATT TAC CGA GCT AAT AGG CTT GTC TCT GGC

GTT CCG TCT CGC TTC AGT GGA AGT GGG AGC GGT ACT

GAT TTT ACC CTC ACC ATA TCA AGC CTT CAA CCG GAG

GAT TTT GCC ACG TAC TAT TGT CTC CAG TAC GAT GAA

TTT CCA TAT ACG TTT GGC GGC GGG ACT CGC TTG GAG

ATT AAA
```

Humanized anti-ROR1 scFv PMC858 amino acid
sequence (SEQ ID NO: 12):
QVQLVESGGGVVQPGRSLRLSCAASGFTFSTYAMSWVRQAPGKGLEWVASISSG

GNTYYPDSVKGRFTISRDNSKNTLYLQMNSLRAEDTAVYYCARDSYYFGNSVYYA

MDYWGAGTTVTVSSGGGGSGGGGSGGGGSDIQMTQSPSSLSASVGDRVTITCKAS

QDINSYFSWFQQKPGKAPKSLIYRANRLVSGVPSRFSGSGSGTDFTLTISSLQPED

FATYYCLQYDEFPYTFGGGTRLEIK

Humanized anti-ROR1 scFv PMC858 VH amino acid
sequence: (SEQ ID NO: 13):
QVQLVESGGGVVQPGRSLRLSCAASGFTFSTYAMSWVRQAPGKGLEWVASIS

SGGNTYYPDSVKGRFTISRDNSKNTLYLQMNSLRAEDTAVYYCARDSYYFGNS

VYYAMDYWGAGTTVTVSS

Humanized anti-ROR1 scFv PMC858 VL amino acid
sequence (SEQ ID NO: 14):
DIQMTQSPSSLSASVGDRVTITCKASQDINSYFSWFQQKPGKAPKSLIYRANRL

VSGVPSRFSGSGSGTDFTLTISSLQPEDFATYYCLQYDEFPYTFGGGTRLEIK

Humanized anti-ROR1 CAR (scFv PMC858) nucleotide
sequence (SEQ ID NO: 37):
ATGGCCTTACCAGTGACCGCCTTGCTCCTGCCGCTGGCCTTGCTGCTCCACG

CCGCCAGGCCGGCTAGCCAGGTACAATTGGTAGAGTCCGGCGGAGGGGTTGTTCAG

CCAGGACGGTCCTTGCGGTTGTCTTGTGCTGCGTCAGGATTCACATTCTCAACGTAC

GCGATGTCTTGGGTGCGCCAAGCTCCCGGTAAAGGGCTGGAATGGGTGGCCTCAAT

CTCATCTGGAGGGAACACTTACTACCCTGATAGTGTTAAAGGTCGCTTTACTATCTC

AAGGGACAATAGCAAGAATACCTTGTATCTGCAAATGAACTCACTTAGAGCAGAGG

ACACAGCGGTATATTACTGTGCTAGAGACTCATATTATTTCGGCAACTCCGTTTATTA

CGCGATGGATTACTGGGGCGCAGGGACTACGGTAACTGTATCTTCTGGTGGTGGAG

GGTCTGGGGGCGGGGGTAGTGGCGGCGGTGGCAGTGACATCCAGATGACACAGTCT

CCGTCTTCATTGAGTGCAAGCGTCGGCGATCGGGTTACCATTACGTGTAAGGCAAGT

-continued

```
CAGGACATCAACAGTTATTTTTCATGGTTTCAACAAAAGCCTGGAAAAGCGCCGAA

ATCACTCATTTACCGAGCTAATAGGCTTGTCTCTGGCGTTCCGTCTCGCTTCAGTGGA

AGTGGGAGCGGTACTGATTTTACCCTCACCATATCAAGCCTTCAACCGGAGGATTTT

GCCACGTACTATTGTCTCCAGTACGATGAATTTCCATATACGTTTGGCGGCGGGACT

CGCTTGGAGATTAAACTCGAGAAGCCCACCACGACGCCAGCGCCGCGACCACCAAC

ACCGGCGCCCACCATCGCGTCGCAGCCCCTGTCCCTGCGCCCAGAGGCGAGCCGGC

CAGCGGCGGGGGCGCAGTGCACACGAGGGGGCTGGACTTCGCCAGTGATAAGCCC

TTTTGGGTGCTGGTGGTGGTTGGTGGAGTCCTGGCTTGCTATAGCTTGCTAGTAACA

GTGGCCTTTATTATTTTCTGGGTGAAACGGGGCAGAAAGAAACTCCTGTATATATTC

AAACAACCATTTATGAGACCAGTACAAACTACTCAAGAGGAAGATGGCTGTAGCTG

CCGATTTCCAGAAGAAGAAGAAGGAGGATGTGAACTGAGAGTGAAGTTCAGCAGG

AGCGCAGACGCCCCCGCGTACCAGCAGGGCCAGAACCAGCTCTATAACGAGCTCAA

TCTAGGACGAAGAGAGGAGTACGATGTTTTGGACAAGAGACGTGGCCGGGACCCTG

AGATGGGGGAAAGCCGCAGAGAAGGAAGAACCCTCAGGAAGGCCTCTACAATGA

ACTGCAGAAAGATAAGATGGCGGAGGCCTACAGTGAGATTGGGATGAAAGGCGAG

CGCCGGAGGGGCAAGGGGCACGATGGCCTTTACCAGGGTCTCAGTACAGCCACCAA

GGACACCTACGACGCCCTTCACATGCAGGCCCTGCCCCCTCGCTAA
```

Humanized anti-ROR1 CAR (scFv PMC858) amino acid
sequence (SEQ ID NO: 15):
MALPVTALLLPLALLLHAARPASQVQLVESGGGVVQPGRSLRLSCAASGFTFS

TYAMSWVRQAPGKGLEWVASISSGGNTYYPDSVKGRFTISRDNSKNTLYLQMNSLRAE

DTAVYYCARDSYYFGNSVYYAMDYWGAGTTVTVSSGGGGSGGGGSGGGGSDIQMTQ

SPSSLSASVGDRVTITCKASQDINSYFSWFQQKPGKAPKSLIYRANRLVSGVPSRFSGSGS

GTDFTLTISSLQPEDFATYYCLQYDEFPYTFGGGTRLEIKLEKPTTTPAPRPPTPAPTIASQ

PLSLRPEASRPAAGGAVHTRGLDFASDKPFWVLVVVGGVLACYSLLVTVAFIIFWVKRG

RKKLLYIFKQPFMRPVQTTQEEDGCSCRFPEEEEGGCELRVKFSRSADAPAYQQGQNQL

YNELNLGRREEYDVLDKRRGRDPEMGGKPQRRKNPQEGLYNELQKDKMAEAYSEIGM

KGERRRGKGHDGLYQGLSTATKDTYDALHMQALPPR

C. PMC862 scFv and CAR
Humanized anti-ROR1 scFv PMC862 nucleotide sequence
(SEQ ID NO: 38):
```
CAG GTA CAA CTG GTG GAA TCC GGC GGG GGA GTA GTA CAG CCC GGA

CGA TCT CTT CGA CTC TCA TGT GCA GCG TCC GGG TTC ACT TTT TCT ACC TAC

GCA ATG TCA TGG GTA CGA CAG GCG CCG GGC AAA GGC CTC GAA TGG GTT GCA

TCC ATT TCA TCA GGA GGT AAT ACA TAT TAT CCT GAT TCA GTC AAG GGC CGA

TTC ACG ATT AGT CGA GAT AAT AGC AAG AAC ACT CTC TAC TTG CAG ATG AAC

TCC CTG CGG GCT GAG GAC ACG GCC GTG TAT TAT TGC GCT CGC GAT AGT TAT

TAC TTC GGC AAT TCC GTA TAT TAT GCG ATG GAC TAT TGG GGC GCC GGT ACT

ACC GTG ACT GTT TCC TCT GGT GGG GGT GGG TCC GGG GGC GGT GGT TCA GGT

GGA GGC GGA TCC GAC ATT CAA ATG ACC CAG TCT CCC TCA AGT TTG TCT GCA

TCT GTT GGC GAT AGA GTT ACA ATA ACA TGC AAA GCC AGT CAA GAC ATC AAC

TCA TAC TTC TCC TGG TAT CAA CAA AAG CCA GGA AAA GCT CCG AAA CTG TTG

ATC TAC CGG GCC AAC CGG CTG GTC ACT GGC GTG CCA TCC CGG TTC AGT GGC
```

```
AGC GGA AGC GGA ACA GAT TTC ACG TTT ACC ATC TCT AGC CTC CAA CCG GAG

GAC ATC GCA ACA TAC TAT TGC CTT CAG TAT GAT GAG TTT CCC TAC ACT TTC

GGT GGC GGC ACC CGA CTT GAG ATC AAA
```

```
Humanized anti-ROR1 scFv PMC862 amino acid sequence
(SEQ ID NO: 16):
QVQLVESGGGVVQPGRSLRLSCAASGFTFSTYAMSWVRQAPGKGLEWVASIS

SGGNTYYPDSVKGRFTISRDNSKNTLYLQMNSLRAEDTAVYYCARDSYYFGNSVYYA

MDYWGAGTTVTVSSGGGGSGGGGSGGGGSDIQMTQSPSSLSASVGDRVTITCKASQDI

NSYFSWYQQKPGKAPKLLIYRANRLVTGVPSRFSGSGSGTDFTFTISSLQPEDIATYYCL

QYDEFPYTFGGGTRLEIK
```

```
Humanized anti-ROR1 scFv PMC862 VH amino acid sequence
(SEQ ID NO: 17):
QVQLVESGGGVVQPGRSLRLSCAASGFTFSTYAMSWVRQAPGKGLEWVASISSG

GNTYYPDSVKGRFTISRDNSKNTLYLQMNSLRAEDTAVYYCARDSYYFGNSVYYA

MDYWGAGTTVTVSS
```

```
Humanized anti-RORI scFv PMC862 VL amino acid sequence
(SEQ ID NO: 18):
DIQMTQSPSSLSASVGDRVTITCKASQDINSYFSWYQQKPGKAPKLLIYRANRL

VTGVPSRFSGSGSGTDFTFTISSLQPEDIATYYCLQYDEFPYTFGGGTRLEIK
```

```
Humanized anti-ROR1 CAR (scFv PMC862) nucleotide sequence
(SEQ ID NO: 39):
ATGGCCTTACCAGTGACCGCCTTGCTCCTGCCGCTGGCCTTGCTGCTCCACG

CCGCCAGGCCGGCTAGCCAGGTACAACTGGTGGAATCCGGCGGGGGAGTAGTACAG

CCCGGACGATCTCTTCGACTCTCATGTGCAGCGTCCGGGTTCACTTTTTCTACCTACG

CAATGTCATGGGTACGACAGGCGCCGGGCAAAGGCCTCGAATGGGTTGCATCCATT

TCATCAGGAGGTAATACATATTATCCTGATTCAGTCAAGGGCCGATTCACGATTAGT

CGAGATAATAGCAAGAACACTCTCTACTTGCAGATGAACTCCCTGCGGGCTGAGGA

CACGGCCGTGTATTATTGCGCTCGCGATAGTTATTACTTCGGCAATTCCGTATATTAT

GCGATGGACTATTGGGCGCCGGTACTACCGTGACTGTTTCCTCTGGTGGGGGTGGG

TCCGGGGGCGGTGGTTCAGGTGGAGGCGGATCCGACATTCAAATGACCCAGTCTCC

CTCAAGTTTGTCTGCATCTGTTGGCGATAGAGTTACAATAACATGCAAAGCCAGTCA

AGACATCAACTCATACTTCTCCTGGTATCAACAAAAGCCAGGAAAAGCTCCGAAAC

TGTTGATCTACCGGGCCAACCGGCTGGTCACTGGCGTGCCATCCCGGTTCAGTGGCA

GCGGAAGCGGAACAGATTTCACGTTTACCATCTCTAGCCTCCAACCGGAGGACATC

GCAACATACTATTGCCTTCAGTATGATGAGTTTCCCTACACTTTCGGTGGCGGCACC

CGACTTGAGATCAAACTCGAGAAGCCCACCACGACGCCAGCGCCGCGACCACCAAC

ACCGGCGCCCACCATCGCGTCGCAGCCCCTGTCCCTGCGCCCAGAGGCGAGCCGGC

CAGCGGCGGGGGCGCAGTGCACACGAGGGGGCTGGACTTCGCCAGTGATAAGCCC

TTTTGGGTGCTGGTGGTGGTTGGTGGAGTCCTGGCTTGCTATAGCTTGCTAGTAACA

GTGGCCTTTATTATTTTCTGGGTGAAACGGGGCAGAAAGAAACTCCTGTATATATTC

AAACAACCATTTATGAGACCAGTACAAACTACTCAAGAGGAAGATGGCTGTAGCTG

CCGATTTCCAGAAGAAGAAGAAGGAGGATGTGAACTGAGAGTGAAGTTCAGCAGG

AGCGCAGACGCCCCCGCGTACCAGCAGGGCCAGAACCAGCTCTATAACGAGCTCAA

TCTAGGACGAAGAGAGGAGTACGATGTTTTGGACAAGAGACGTGGCCGGGACCCTG

AGATGGGGGAAAGCCGCAGAGAAGGAAGAACCCTCAGGAAGGCCTCTACAATGA
```

```
ACTGCAGAAAGATAAGATGGCGGAGGCCTACAGTGAGATTGGGATGAAAGGCGAG

CGCCGGAGGGGCAAGGGGCACGATGGCCTTTACCAGGGTCTCAGTACAGCCACCAA

GGACACCTACGACGCCCTTCACATGCAGGCCCTGCCCCCTCGCTAA

Humanized anti-ROR1 CAR (scFv PMC862) amino acid sequence
(SEQ ID NO: 19):
MALPVTALLLPLALLLHAARPASQVQLVESGGGVVQPGRSLRLSCAASGFTFS

TYAMSWVRQAPGKGLEWVASISSGGNTYYPDSVKGRFTISRDNSKNTLYLQMNSLRAE

DTAVYYCARDSYYFGNSVYYAMDYWGAGTTVTVSSGGGGSGGGGSGGGGSDIQMTQ

SPSSLSASVGDRVTITCKASQDINSYFSWYQQKPGKAPKLLIYRANRLVTGVPSRFSGSG

SGTDFTFTISSLQPEDIATYYCLQYDEFPYTFGGGTRLEIKLEKPTTTPAPRPPTPAPTIA

SQPLSLRPEASRPAAGGAVHTRGLDFASDKPFWVLVVVGGVLACYSLLVTVAFIIFWVKRG

RKKLLYIFKQPFMRPVQTTQEEDGCSCRFPEEEEGGCELRVKFSRSADAPAYQQGQNQL

YNELNLGRREEYDVLDKRRGRDPEMGGKPQRRKNPQEGLYNELQKDKMAEAYSEIGM

KGERRRGKGHDGLYQGLSTATKDTYDALHMQALPPR
```

Example 5. Producing the CAR Using Lentiviral Vectors

In this example, CARs containing the three humanized scFvs of Example 4 were packaged into lentiviral vectors. The lentiviruses were produced by the standard procedure using HEK293 cells as described in Goluboskaya et al., (2016) Different Subsets of T Cells, Memory, Effector Functions, and CAR-T Immunotherapy. Cancers (Basel). 2016 Mar. 15; 8(3). pii: E36.

Example 6. Peripheral Blood Mononuclear Cell (PBMC) Isolation from Whole Blood In this example PBMCs were isolated from whole blood for the purpose of producing CAR-T cells. Whole blood (Stanford Hospital Blood Center, Stanford, Cal.) was collected from individuals or mixed-donor samples (depending on the amount of blood required) in 10 mL heparin vacutainers (Becton Dickinson, San Jose, Cal.). Approximately 10 ml of whole anti-coagulation-treated blood was mixed with sterile phosphate buffered saline (PBS pH 7.4, $Ca^{2+}$ and $Mg^{2+-}$ free) for a total volume of 20 ml in a 50 ml conical centrifuge tube. The layer of cells containing PBMCs seen at the diluted plasma/Ficoll interface was removed very carefully, avoiding any Ficoll, washed twice with PBS, and centrifuged at 200×g for 10 min at room temperature. Cells were counted with a hemocytometer. The PBMCs were washed once with CAR-T medium (AIM V-AlbuMAX (BSA) (Life Technologies, San Diego, Cal.) with 5% AB serum and 1.25 ug/mL amphotericin B (Gemini Bioproducts, Woodland, Cal.), 100 U/mL penicillin, and 100 ug/mL streptomycin and used for experiments or frozen at −80° C.

Example 7. T-Cell Activation from PBMC

Isolated PBMC were washed with once 1×PBS (pH7.4, no $Ca^{2+}/Mg^{2+}$), and in CAR-T medium (Example 6), in the absence of human interleukin-2 (huIL2) at a concentration of $5×10^5$ cells/mL, then resuspended to a final concentration of $5×10^5$ cells/mL in CAR-T medium with 300 U/mL huIL2 (from a 1000×stock; Invitrogen, Carlsbad, Cal.). PBMC and beads (for T cell activation) were then mixed at a 1:1 bead-to-cell ratio, by transferring 25 uL of beads to 1 mL of PBMC and incubated at 37° C. in the presence of $CO_2$ for 24 hr before viral transduction.

Example 8. T-Cell Transduction and Expansion

Following activation of PBMC, $5×10^6$ lentiviruses were added to $5×10^5$ T cells (MOI 10:1), and 2 µL/mL of media of Transplus (Alstem, Richmond, Cal.) to final dilution of 1:500. The cells were incubated for an additional 24 hours before repeating the addition of virus. The cells were then grown in the presence of 300 U/mL of IL-2 for a period of 12-14 days (total incubation time was dependent on the final umber of CAR-T cells required). Cell numbers were analyzed every 2-3 days, with media being added at that time to dilute the cell suspension to $1×10^6$ cells/ml.

Example 9. Transduction of T Cells and CAR Verification by FACS

The cells from Example 8 were washed and suspended in FACS buffer (PBS plus 0.1% sodium azide and 0.4% BSA). Cells were then divided into $1×10^6$ cell aliquots. Fc receptors were blocked with normal goat IgG (Life Technologies, San Diego, Cal.). Biotin-labeled polyclonal goat anti-mouse $F(ab)_2$ antibodies were used to detect mouse anti-ROR1 scFv; biotin-labeled normal polyclonal goat IgG antibodies also served as an isotype control. The cells were incubated at 4° C. for 25 minutes and washed once with FACS buffer. After staining the cells with anti-$F(ab)_2$ antibody, phycoerythrin (PE)-labeled streptavidin (BD Pharmingen, San Diego, Cal.) and allophycocyanin (APC)-labeled CD3 (eBiocience, San Diego, Cal.) were used to stain the cells. For humanized anti-ROR1 scFv we also used anti-human $F(ab)_2$ antibodies (Life Technologies).

Example 10. Real-Time Cytotoxicity Assay

The cytotoxicity was performed using xCELLigence real-time cell analysis system (Agilent, San Jose, Cal.), according to the manufacturer's protocol as described in Berahovich et al., (2018) CAR-T cells based on Novel BCMA monoclonal antibody block multiple myeloma Cell growth. Cancers (Basel) (9).

Figure 5A:
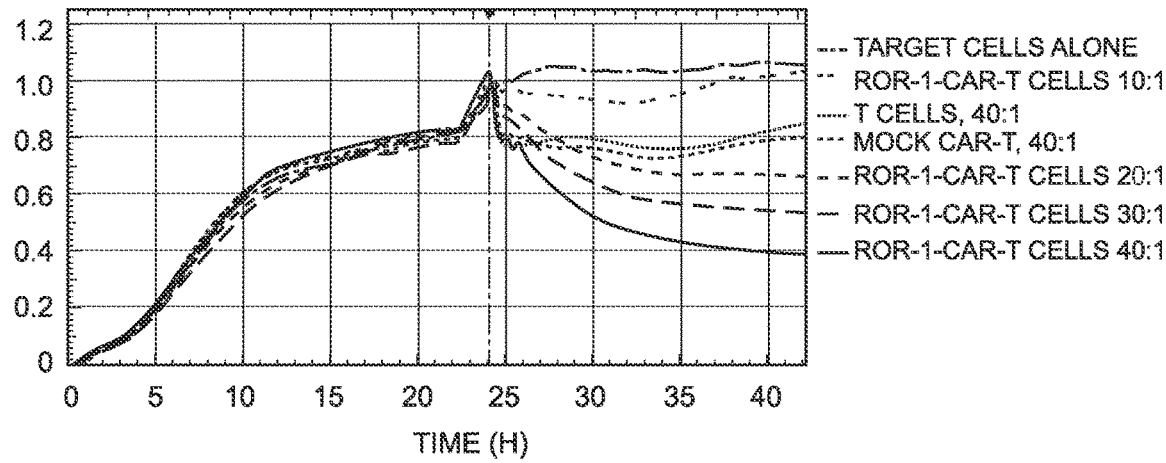
FIG. 5A shows an RTCA assay demonstrating dose-dependent cytotoxicity of anti-ROR1 CAR-T cells (ROR1-CD28-CD against the ROR1-expressing cell line SKOV-3.

Example 11. CAR-T Cells with Mouse Anti-ROR1 scFv Expressed High Cytotoxic Activity Against ROR1-Positive Cancer Cells Expression of mouse-scFv anti-ROR1 CAR was confirmed by FACS with anti-mouse Fab antibodies. The CAR-T cells with the CAR containing the mouse anti-ROR1 scfv, CD28 costimulatory domain and CD3 zeta activation domain (see Example 3(A)) were used in this cytotoxicity assay. The cytotoxicity assay was performed using RTCA impedance-based assay on the xCELLigence system according to manufacturer's conditions. In this assay, the integrity of the target cell monolayer is continually monitored via its impedance in a weak electrical field. Killing of the target cells by the CAR-T cells decreases the monolayer's integrity and, therefore, its impedance. The anti-ROR1 CAR-transduced T cells were added to the target cells at effector:target (E:T) ratios of 10:1, 20:1, 30:1, and 40:1 (FIG. 5A). The CAR-T cells caused a sustained dose-dependent decrease in target cell monolayer impedance. Thus, anti-ROR1-CD28-CD3 CAR-T cells killed the ROR1 positive SKOV-3 ovarian solid tumor cells in a dose-dependent manner.

Figure 5B:
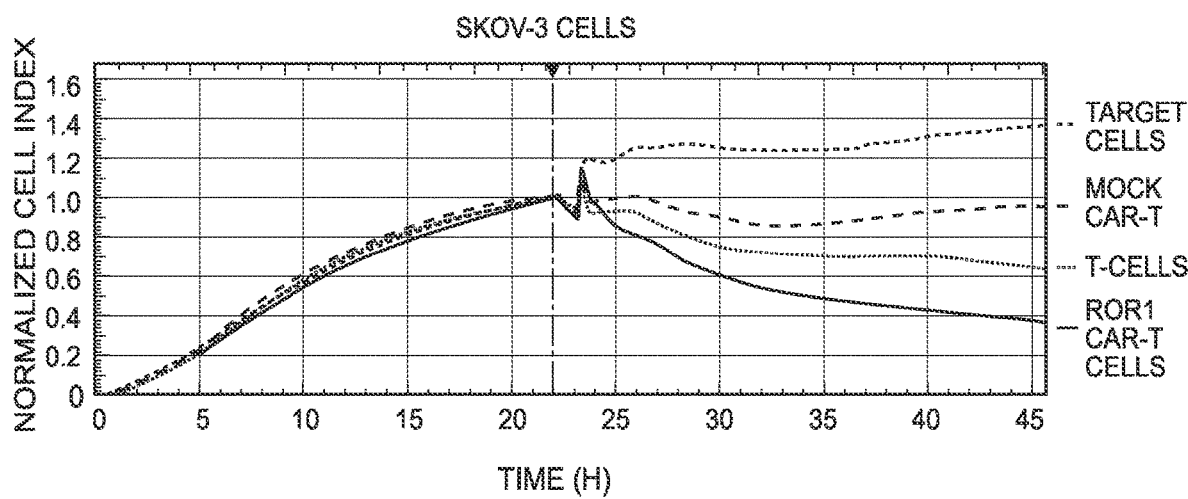
FIG. 5B shows an RTCA assay demonstrating dose-dependent cytotoxicity of anti-ROR1 CAR-T cells ROR1-4-1BB-CD3 against the ROR1-expressing cell line SKOV-3.

Similar high cytotoxic activity was observed also with CAR-T cells with the CAR containing the mouse anti-ROR1 scfv, 4-1BB costimulatory domain and CD3 zeta activation (Example 3(B)) and ROR1-positive SKOV-3 target cells (FIG. 5B).

Figure 6:
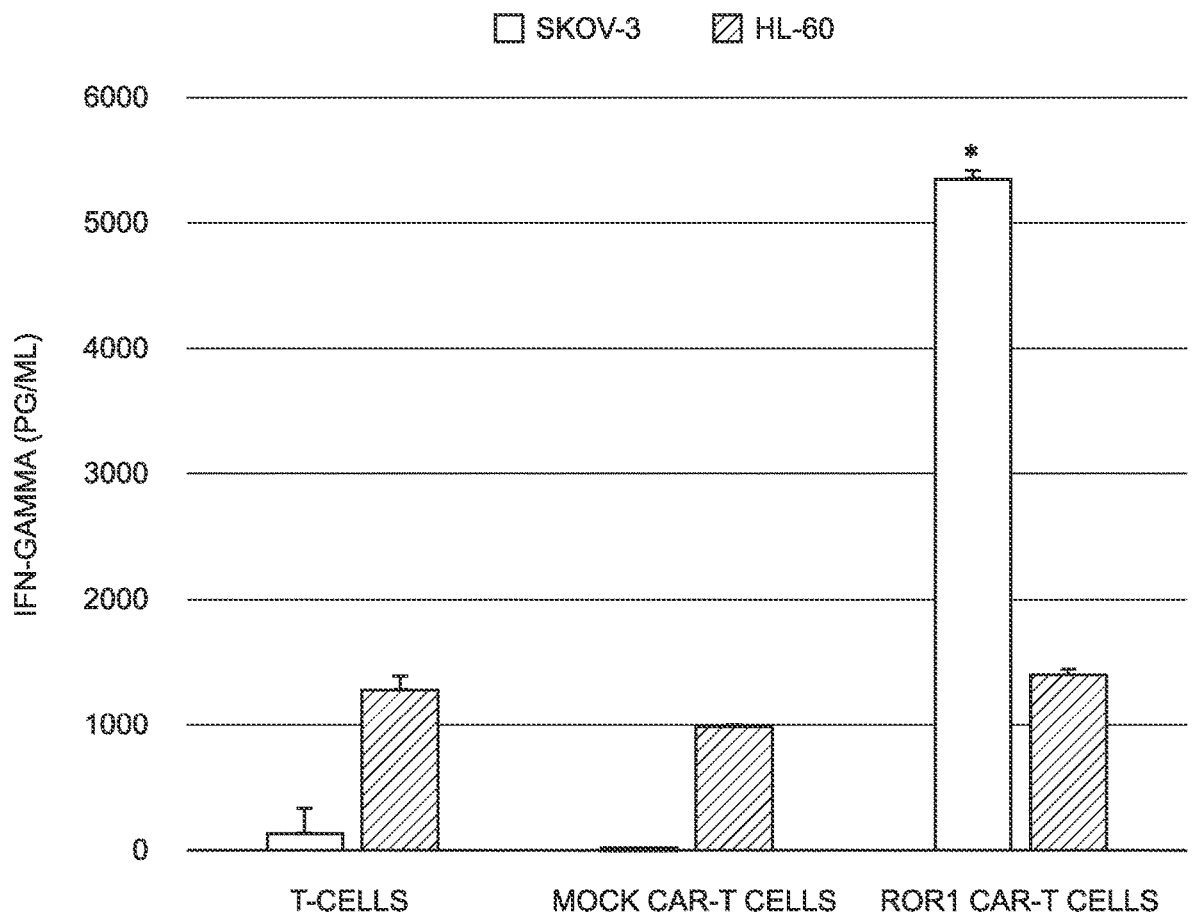
FIG. 6 shows measurements of IFN-gamma secretion by anti-ROR1 CAR-T cells (ROR1-4-1BB-CD3) in the presence of SKOV-3 cells or control HL-60 cells (ROR1-negative cells).

Example 12. Anti-ROR1-CAR T Cells (Mouse scFv) Secrete High Level of IFN-Gamma in the Presence of ROR1-Positive Cancer Cells After co-incubation of ROR1-41BB-CD3-CAR-T cells with SKOV-3 cells, we collected the supernatant and performed ELISA with a commercial kit (ThermoFisher Scientific, Waltham, Mass.). As a control we used non-adherent HL-60 ROR1-negative cell line. The anti-ROR1-CAR-T cells secreted significantly higher level of IFN-gamma in the presence of ROR1-positive SKOV-3 cancer cells than in the presence of ROR1-negative control cells, and in comparison to T cells and mock CAR-T cells used as control (P<0.05). (FIG. 6).

Figure 7:
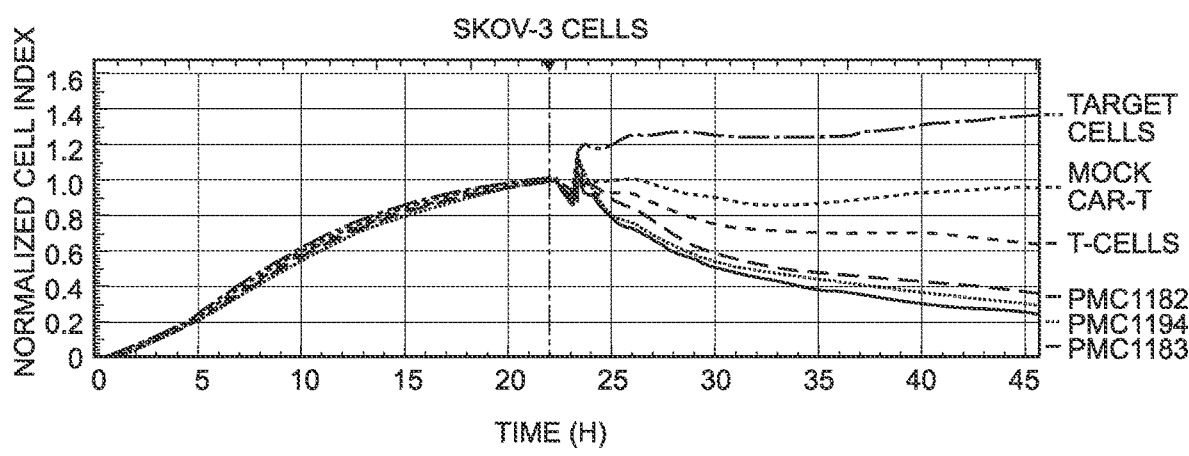
FIG. 7. shows an RTCA assay demonstrating dose-dependent in vitro cytotoxicity of the anti-ROR1 CAR-T cells with humanized scFvs (PMC1182, PMC1183 and PMC1194 expressing PMC857, PMC858, and PMC862 anti-ROR1 CARs respectively) against SKOV3 cells.

Example 13. Anti-ROR1-CAR T Cells (Humanized scFv) Exhibited Cytotoxicity and Secreted High Level of IFN-Gamma in the Presence of ROR1-Positive Cancer Cells First we tested CAR-T cells with scFvs PMC857, PMC868, or PMC862 (Example 5) in a cytotoxic assay with ROR1-positive cells and showed that the CAR-T cells were highly cytotoxic. Next, we inserted these CAR constructs (PMC857, PMC868, or PMC862) into lentiviral vectors with KanR gene (preferred for clinical usage) instead of AmpR gene. The CAR-T cell clones became clones PMC1182, 1183 and 1194, respectively. The CAR expression in CAR-T cells was about 30% CAR+ as detected by FACS with human Fab. We performed RTCA assay and detected high cytotoxic activity of these CAR-T cells against SKOV-3 (ROR1-positive) cells (FIG. 7).

Figure 8:
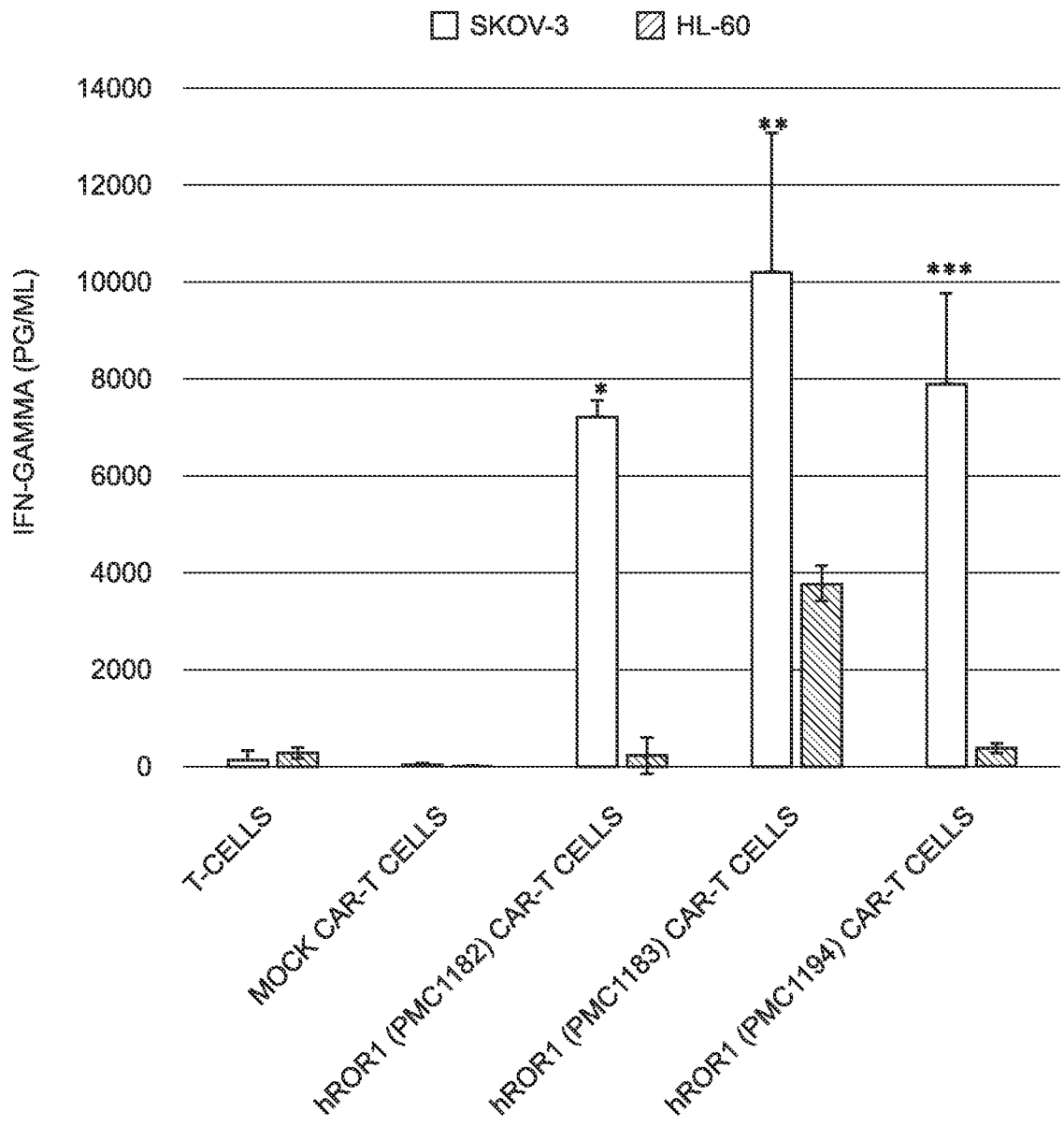
FIG. 8. shows measurements of IFN-gamma secretion by the anti-ROR1 CAR-T cells with humanized scFvs (PMC1182, PMC1183 and PMC1194 expressing PMC857, PMC858, and PMC862 anti-ROR1 CARs respectively) in the presence of SKOV-3 cells or control HL-60 cells.

Next we assessed cytokine secretion by the CAR-T cells. After co-incubation of the CAR-T cells with SKOV-3 cells, we collected the culture supernatant and performed ELISA to detect Interferon-Gamma in the supernatant as described in Example 12 using the non-adherent HL-60 ROR1-negative cell line as a control. The anti-ROR1-CAR-T cells secreted significantly higher level of IFN-gamma in the presence of ROR1-positive SKOV-3 cancer cells than in the presence of ROR1-negative control cells, and in comparison to T cells and mock CAR-T cells used as control (P<0.05). (FIG. 8).

While the invention has been described in detail with reference to specific examples, it will be apparent to one skilled in the art that various modifications can be made within the scope of this invention. Thus, the scope of the invention should not be limited by the examples described herein, but by the claims presented below.

---

What is claimed is:

1. An anti-human ROR1 antibody or an antigen-binding fragment thereof comprising $V_H$ having an amino acid sequence at least 90% identical to SEQ ID NO: 2 and $V_L$ having an amino acid sequence at least 90% identical to SEQ ID NO: 3, the antibody or antigen-binding fragment comprising complementarity determining regions (CDRs) in the $V_H$ and the $V_L$, wherein a CDR1 of the $V_H$ comprises the sequence TYA, a CDR2 of the $V_H$ comprises SEQ ID NO: 41, a CDR3 of the $V_H$ comprises SEQ ID NO: 42, a CDR1 of the $V_L$ comprises SEQ ID NO: 43, a CDR2 of the $V_L$ comprises the sequence RAN, and a CDR3 of the $V_L$ comprises SEQ ID NO: 45.

2. The anti-human ROR1 antibody or an antigen-binding fragment thereof of claim 1, comprising a humanized mouse amino acid sequence.

3. The anti-human ROR1 antibody or an antigen-binding fragment thereof of claim 2, wherein the antigen-binding fragment is a single-chain variable fragment (scFv).

4. The scFv of claim 3, comprising a $V_H$ comprising SEQ ID NO: 17, a $V_L$ comprising SEQ ID NO: 18, and a linker.

5. The scFv of claim 4, comprising a $V_H$ consisting of SEQ ID NO: 17, a $V_L$ consisting of SEQ ID NO: 18, and a linker.

6. The scFv of claim 3, encoded by a nucleic acid comprising SEQ ID NO: 38.

7. A chimeric antigen receptor (CAR) comprising the scFv of claim 3 and further comprising: a transmembrane domain, at least one co-stimulatory domains, and an activation domain.

8. The CAR of claim 7, wherein the co-stimulatory domain is CD28 or 4-1BB.

9. The CAR of claim 7, wherein the activation domain is CD3 zeta.

10. The CAR of claim 7, wherein the transmembrane domain is a CD8 transmembrane domain.

11. The CAR of claim 7, further comprising a signaling peptide and a hinge domain.

12. The CAR of claim 11, wherein the signaling peptide and the hinge domain are the CD8 signaling peptide and the CD8 hinge domain.

13. The CAR of claim 7, comprising the amino acid sequence of SEQ ID NO: 19.

14. The CAR of claim 13, consisting of the amino acid sequence of SEQ ID NO: 19.

15. The CAR of claim 7, encoded by a nucleic acid comprising sequence of SEQ ID NO: 39.

16. An engineered immune cell expressing the CAR of claim 7.

17. The engineered immune cell of claim 16, wherein the cell is selected from a CAR-T cell and a CAR-NK (natural killer) cell.

18. A composition comprising the engineered immune cell of claim 16 and an excipient.

* * * * *

UNITED STATES PATENT AND TRADEMARK OFFICE
CERTIFICATE OF CORRECTION

PATENT NO. : 11,932,703 B2
APPLICATION NO. : 18/321655
DATED : March 19, 2024
INVENTOR(S) : Vita Golubovskaya and Lijun Wu It is certified that error appears in the above-identified patent and that said Letters Patent is hereby corrected as shown below:

In the Claims

Column 45 Claim 1, Line 47:
Delete "SEO ID NO: 42" and insert --SEQ ID NO: 42--

Signed and Sealed this
Eighteenth Day of June, 2024

Katherine Kelly Vidal
*Director of the United States Patent and Trademark Office*